(12) United States Patent
Klaveness et al.

(10) Patent No.: US 7,834,010 B2
(45) Date of Patent: Nov. 16, 2010

(54) MODULATORS OF PERIPHERAL 5-HT RECEPTORS

(75) Inventors: Jo Klaveness, Oslo (NO); Finn Olav Levy, Oslo (NO); Bjarne Brudeli, Oslo (NO)

(73) Assignee: Serodus AS, Oslo (NO)

( * ) Notice: Subject to any disclaimer, the term of this patent is extended or adjusted under 35 U.S.C. 154(b) by 792 days.

(21) Appl. No.: 10/583,829

(22) PCT Filed: Dec. 23, 2004

(86) PCT No.: PCT/NO2004/000399

§ 371 (c)(1), (2), (4) Date: Apr. 5, 2007

(87) PCT Pub. No.: WO2005/061483

PCT Pub. Date: Jul. 7, 2005

(65) Prior Publication Data

US 2007/0254874 A1  Nov. 1, 2007

(30) Foreign Application Priority Data

Dec. 23, 2003 (DK) ................................. 2003 01924

(51) Int. Cl.
*A61K 31/536* (2006.01)
*C07D 265/12* (2006.01)

(52) U.S. Cl. .................... 514/230.2; 544/89
(58) Field of Classification Search .............. 514/230.2; 544/89
See application file for complete search history.

(56) References Cited

U.S. PATENT DOCUMENTS

| 4,494,547 | A | 1/1985 | Myers |
| 6,552,004 | B1 | 4/2003 | Elazhary et al. |
| 6,552,046 | B2 | 4/2003 | Druzgala et al. |
| 6,624,163 | B2 | 9/2003 | Flohr et al. |
| 6,632,827 | B2 | 10/2003 | McCullough et al. |

| 2001/0031751 | A1 | 10/2001 | Bush et al. |
| 2003/0019386 | A1 | 1/2003 | Lloyd et al. |

FOREIGN PATENT DOCUMENTS

| EP | 1 149 832 | 10/2001 |
| JP | 11-292846 | 10/1999 |
| WO | WO 93/18036 | 9/1993 |
| WO | WO 96/10027 | 4/1996 |
| WO | WO 01/93849 | 12/2001 |

OTHER PUBLICATIONS

International Search Report for International Application No. PCT/NO2004/000399 dated Aug. 17, 2005.
Muller-Lissner, et al. "Tegaserod, a 5-HT$_4$ receptor partial agonist, relieves symptoms in irritable bowel syndrome patients with abdominal pain, bloating and constipation." Aliment Pharmacol Ther. 15:1655-1666 (2001).
Mutschler, et al. "Arzneimittelwirkungen." WYG, Stuttgart. 462-466 (2001).
Sanger, et al. "SB-207266: 5-HT$_4$ receptor antagonism in human isolated gut and prevention of 5-HT-evoked sensitization of peristalsis and increased defaecation in animal models." Neurogastroenterol. Mot. 10:271-279 (1998).
Awapara, Jorge. "2-Aminoethanesulfinic Acid: An Intermediate in the Oxidation of Cysteine in vivo." Journal of Biological Chemistry. 183-188 (1952).
Weller et al. "The Detection of 3-Indoleacetic Acid in Cauliflower Heads. Chromatographic Behavior of Some Indole Compounds." 76: 629-630 (1954).
Karl-Heinz et al. "The Serotonin 5-Ht$_4$ Receptor. 2. Structure-Activity Studies of the Indole Carbazimidamide Class of Agonists." J. Med. Chem. 38:2331-2338 (1995).
Kato, Hideo et al. "Preparation of benzamidopiperidinocarboxylates and pharmaceuticals for treatment of digestive system disease." Abstract. Jan. 31, 2001.

*Primary Examiner*—Taofiq A Solola
(74) *Attorney, Agent, or Firm*—Knobbe Martens Olson & Bear LLP

(57) ABSTRACT

The invention relates to modulators of peripheral 5-HT receptors, particularly 5-HT4 receptors, said modulators essentially selective for peripheral 5-HT receptors over receptors of the central nervous system. The invention allows for the treatment, amongst others, of gastrointestinal disorders, lower urinary tract disorders, and cardiovascular disorders without side effects related to CNS activity.

7 Claims, No Drawings ns and partial agonists. Modulators of 5-HT$_4$ receptors are
MODULATORS OF PERIPHERAL 5-HT RECEPTORS

CROSS-REFERENCE TO RELATED APPLICATIONS

This application is a U.S. National Phase Application under 35 U.S.C. §371 of International Patent Application No.: PCT/NO2004/000399, filed Dec. 23, 2004 designating the United States of America, and published in English on Jul. 7, 2005, which claims priority to Denmark Patent Application No.: PA 2003 01924, filed Dec. 23, 2003, all of which are hereby expressly incorporated by reference in their entireties.

FIELD OF THE INVENTION

The invention relates to modulators of peripheral 5-HT receptors, particularly 5-HT4, receptors said modulators essentially selective for peripheral 5-HT receptors over receptors of the central nervous system. The invention allows for the treatment, amongst others, of gastrointestinal disorders, lower urinary tract disorders, and cardiovascular disorders without side effects related to CNS activity.

BACKGROUND OF THE INVENTION

5-Hydroxytryptamine (5-HT) is an important signalling molecule in the human body, and has important effects both as a neurotransmitter and as a locally acting signalling molecule with e.g. vasoactive effects. During the past 20 years 14 different 5-HT receptors have been identified and classified into 7 different subgroups (5-HT$_1$, 5-HT$_2$, 5-HT$_3$, 5-HT$_4$, 5-HT$_5$, 5-HT$_6$ and 5-HT$_7$), based on structural and pharmacological criteria as well as signal transduction properties. Additional diversity arises from e.g. alternative splicing of e.g. 5-HT$_4$ (e.g. 5-HT$_{4(a)}$, 5-HT$_{4(b)}$ etc.) and 5-HT$_7$ receptors, and of RNA editing of e.g. 5-HT$_{2C}$ receptors. 5-HT$_4$ is found to play a central role in diseases in organs like the heart, the gastrointestinal system, the urinary bladder and central nervous system (CNS).

5-HT$_4$ receptor modulators, agonists and antagonists alike, are found to be useful for the treatment of a variety of diseases such as gastroesophageal reflux disease, gastrointestinal disease, gastric motility disorder, non-ulcer dyspepsia, functional dyspepsia, irritable bowel syndrome, constipation, dyspepsia, oesophagitis, gastroesophageal disease, nausea, central nervous system disease, Alzheimer's disease, cognitive disorder, emesis, migraine, neurological disease, pain, and cardiovascular disorders such as cardiac failure and heart arrhythmia. Further gastrointestinal disorders suitable for prophylaxis or treatment of the symptoms of Irritable Bowel Syndrome, including abdominal pain and disrupted colonic motility.

Since 5-HT$_4$ receptors are located both inside and outside the CNS, 5-HT$_4$ receptor agonists and antagonists will have effects both inside and outside the CNS, unless their design prevents their access to or causes them to preferentially localise to only one of these compartments. When addressing 5-HT$_4$ receptors located outside the CNS, effects on receptors inside the CNS may represent undesirable side-effects of the treatment, and vice versa. The present invention seeks to avoid this problem by presenting 5-HT$_4$ receptor agonists and antagonists which will not penetrate the blood-brain barrier and thus will not have access to 5-HT$_4$ receptors located inside the CNS.

Moreover, the problem of poor targeting of 5-HT receptor ligands is aggravated by the fact that the receptor activity is diminished upon frequent binding. Unwanted or unselective binding is undesired in this context also.

Several modulators with affinity for 5-HT$_4$ receptors are known in the state of the art. This includes agonists, antagonists and partial agonists. Modulators of 5-HT$_4$ receptors are today in active development as potential therapeutic drugs.

U.S. Pat. No. 6,552,046 discloses the modification of the piperidinyl nitrogen of cisapride with a moiety wherein an acidic group may be in close proximity to the basic nitrogen. Moreover, despite recognising that cisapride has CNS side effects, it modifies cisapride with an ester moiety for purposes of avoiding cytochrome P-450 due to degradation of the ester by esterases. Most remarkably, U.S. Pat. No. 6,552,046 observes that cisapride enters the central nervous system and binds to 5-HT4 receptors, indicating that cisapride may have centrally-mediated effects. It further states compounds of U.S. Pat. No. 6,552,046 can be used in the treatment of: 1) cognitive disorders, including but not limited to Alzheimer's disease; 2) behavioural disorders, including but not limited to schizophrenia, mania, obsessive- compulsive disorder, and psychoactive substance use disorders; 3) mood disorders, including but not limited to depression and anxiety; and 4) disorders of control of autonomic function, including but not limited to essential hypertension and sleep disorders.

U.S. Pat. No. 6,624,163 (Pfizer) discloses imidazopyridines as 5-HT$_4$ modulators. Notably, none of the embodiments of the invention comprise an acidic moiety. This recent attempt in the area of 5-HT modulators is silent to means of differentiation between 5-HT related CNS disorders to gastrointestinal or cardiac disorders. The novel compounds are directed to everything from neurological diseases to heartburn. Each of the embodiments of U.S. Pat. No. 6,624,163 are suitable substrates for modification with an acidic moiety according to the present invention.

U.S. Pat. No. 6,632,827 seeks to minimise side effects with the use of an optically pure form of norcisapride in the treatment of gastrointestinal disorders yet concerns itself with the associated serious CNS side effects such as memory loss, sleep disorders, depression, and psychoactive distress. Each of the embodiments of U.S. Pat. No. 6,632,827 are suitable substrates for modification with an acidic moiety according to the present invention US 2001/0031751 provides novel 5-HT4 antagonists, but does not seek to differentiate the CNS-from the peripherally-located receptors and thus intends their use in both CNS and gastrointestinal or cardiovascular disorders. Notably, none of the embodiments of the invention comprise an acidic moiety. Each of the embodiments of US 2001/0031751 are suitable substrates for modification with an acidic moiety according to the present invention.

SUMMARY OF THE INVENTION

A principal object of the invention is providing 5-HT$_4$ receptor modulators selective to peripheral receptors, essentially to the exclusion of delivery to CNS located receptors. The invention accomplishes this by modifying existing modulators and allows for the design and preparation of new modulators which comprise an acidic moiety so that the modulator is unable to cross the blood-brain barrier.

An essential feature of 5-HT modulators, particularly 5-HT4 modulators, is the presence of a basic nitrogen (termed BN in formulas of the invention). The present inventors have found that the presence of an acidic moiety, particularly one wherein the acidic hydrogen of the acidic moiety is at least 2 atoms from the basic nitrogen, dramatically improves the selectivity of these modulators for peripheral 5-HT receptors compared to those of the central nervous system. The present inventors have modified existing 5-HT modulators and prepared entirely novel 5-HT modulators which, due to comprising both an acidic moiety and a basic nitrogen, will provide for improved treatment of conditions affected by modulating of peripheral 5-HT receptors and with reduced side effects, due to the selectivity over receptors of the central nervous system.

A general aspect of the invention relates to the treatment of a disease associated, at least in part, with peripheral 5-HT receptor comprising administering a compound of the invention, preferably with a peripheral 5-HT4 receptor, preferably essentially whilst not modulating a 5-HT receptor of the central nervous system.

The invention relates to a compound which fulfils the following: i) a binding affinity to a 5-HT receptor with a $pK_i$ of at least 5; ii) comprises at least one basic nitrogen atom; iii) comprises at least one acidic moiety with a pKa of no more than 6.4, or a salt or ester thereof.

A further aspect of the invention relates to a compound having a binding $pK_i$ for a 5-HT receptor of at least 5 and is of the formula I

BN-L-A                                            I wherein BN is a basic nitrogen moiety; and
-A is an acidic moiety with a pKa of no more than 6.4 or an ester thereof;
wherein BN-L-A comprises at least 3 consecutive chemical bonds between BN and the acidic moiety.

An important aspect of the invention relates to compound of formula II,

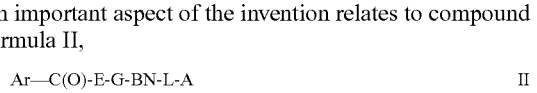

Ar—C(O)-E-G-BN-L-A                                II wherein Ar is selected from the group consisting of an optionally substituted aryl ring, an optionally substituted aryl ring fused with one or more non-aromatic optionally substituted carbocylic rings, an optionally substituted aryl ring fused with one or more optionally substituted non-aromatic heterocyclic rings, an optionally substituted aryl ring fused with one or more optionally substituted aromatic or heteroaromatic rings, C(O) is absent or a carbonyl carbon;
E is absent or selected from the group consisting of O and NH;
G is absent or selected from the group consisting of $C_{1-6}$-alkyl, $C_{3-7}$-cycloalkyl, $C_{1-6}$-alkyl-$C_{3-7}$-cycloalkyl, $C_{3-7}$-cycloalkyl-$C_{1-6}$-alkyl;
wherein BN is a basic nitrogen moiety selected from the group consisting of an amine group, an amide group, a carbamate or a carbamate derivative, urea or a urea derivative, a carbazimidamide, a nitrogen-containing heterocyclic, a nitrogen-containing heteroarylic ring, and an azabicyclic ring;
L is absent or selected from the group consisting of a straight chain or branched optionally substituted $C_{1-10}$-alkyl, optionally substituted $C_{2-10}$-alkenyl, optionally substituted $C_{2-10}$-alkynyl, $C_{1-10}$-alkylamine, $C_{1-10}$-alkoxy, $C_{2-10}$-alkenyloxy, $C_{2-10}$-alkynyloxy, $C_{1-10}$-alkoxycarbonyl, $C_{2-10}$-alkenyloxycarbonyl, $C_{2-10}$-alkynyloxycarbonyl or combinations thereof; and
A is selected from the group consisting of $C(O)$—$OR^1$, $OP(O)OR^2OR^2$, $P(O)OR^2OR^2$, $SO_2OR^2$, $SO_3H$, $OSO_3H$, and $PO_3H$; wherein $R^1$ and $R^2$ are independently selected from the group consisting of H, M, $C_{1-15}$-alkyl, $C_{3-8}$-cycloalkyl, aryl, and $R^{1,2}$ wherein $R^{1,2}$ is R'—O—C(O)—R", R'—O—C(O)—O—R", R'—C(O)—O—R", wherein R' and R" are independently selected from the group consisting of $C_{1-15}$-alkyl, $C_{3-8}$-cycloalkyl and aryl.

An interesting embodiment of the compounds of the invention is a compound according of the formula IV-P

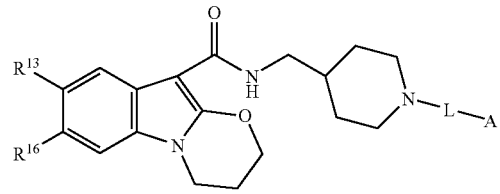

IV-P wherein L is absent or selected from the group consisting of straight chain or branched optionally substituted $C_{1-10}$-alkyl, optionally substituted $C_{2-10}$-alkenyl, optionally substituted $C_{2-10}$-alkynyl, $C_{1-10}$-alkylamine, $C_{1-10}$-alkoxy, $C_{2-10}$-alkenyloxy, $C_{2-10}$-alkynyloxy, $C_{1-10}$-alkoxycarbonyl, $C_{2-10}$-alkenyloxycarbonyl, $C_{2-10}$-alkynyloxycarbonyl; and A is selected from the group consisting of —C(O)—$OR^1$, —OP(O)$OR^2OR^2$, —P(O)$OR^2OR^2$, —$SO_2OR^2$, and $PO_3H$; wherein $R^1$ and $R^2$ are independently selected from the group consisting of H, M, $C_{1-15}$-alkyl, $C_{3-8}$-cycloalkyl, aryl, and $R^{1,2}$ wherein $R^{1,2}$ is R'—O—C(O)—R", R'—O—C(O)—O—R", R'—C(O)—O—R", wherein R' and R" are independently selected from the group consisting of $C_{1-15}$-alkyl, $C_{3-8}$-cycloalkyl and aryl;

$R^{13}$ is selected from the group consisting of H, halogen, $NH_2$, and $C_{1-6}$-alkyl; and $R^{16}$ is selected from the group consisting of H, halogen, OH, O—$C_{1-6}$-alkyl, and $C_{1-6}$-alkyl.

A particularly interesting embodiment of compounds of the formula II are compounds of formula VI,

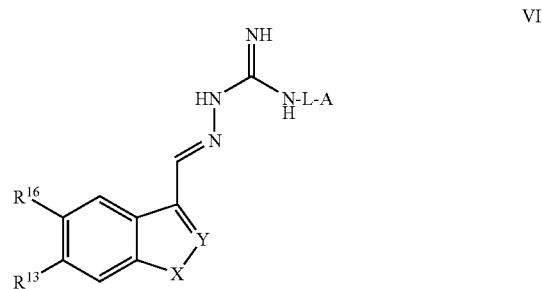

VI wherein X and Y are independently selected from the group consisting of NH, O, C, and S;

L is absent or selected from the group consisting of straight chain or branched optionally substituted $C_{1-10}$-alkyl, optionally substituted $C_{2-10}$-alkenyl, optionally substituted $C_{2-10}$-alkynyl, $C_{1-10}$-alkylamine, $C_{1-10}$-alkoxy, $C_{2-10}$-alkenyloxy, $C_{2-10}$-alkynyloxy, $C_{1-10}$-alkoxycarbonyl, $C_{2-10}$-alkenyloxycarbonyl, $C_{2-10}$-alkynyloxycarbonyl;

A is selected from the group consisting of —C(O)—$OR^1$, —OP(O)$OR^2OR^2$, —P(O)$OR^2OR^2$, —$SO_2OR^2$, and $PO_3H$; wherein $R^1$ and $R^2$ are independently selected from the group consisting of H, M, $C_{1-15}$-alkyl, $C_{3-8}$-cycloalkyl, aryl, and $R^{1,2}$ wherein $R^{1,2}$ is R'—O—C(O)—R", R'—O—C(O)—O—R", R'—C(O)—O—R", wherein R' and R" are independently selected from the group consisting of $C_{1-15}$-alkyl, $C_{3-8}$-cycloalkyl and aryl;

and $R^{16}$ and $R^{13}$ are independently selected from the group consisting of H, OH, halogen, $NH_2$, O—$C_{1-6}$-alkyl, and $C_{1-6}$-alkyl.

A further aspect of the invention relates to a method of treating a cardiovascular disorder comprising administering a compound of the invention. Suitably, the cardiovascular disorder is selected from tachycardia, bradycardia, cardioexcitation, cardiodepression, arrhythmia, fibrillation, atrial fibrillation, Paroxysmal Supraventricular Tachycardia (PSVT), thromoembolisms and VTE.

A particularly interesting aspect of the invention relates to a method of treating gastrointestinal disorders, such as irritable bowel syndrome, comprising administering a compound of the invention. Alternatively stated, an aspect of the invention relates to the use of the compounds of the invention for the preparation of a medicament for the prophylaxis or treatment of gastrointestinal disorders suitable and for symptoms of Irritable Bowel Syndrome, including abdominal pain and disrupted colonic motility; diarrhea; constipation; urinary incontinence and anal incontinence The treatment of lower urinary tract disorders, such as e.g. hyperactive bladder, comprising administering a compound of the invention is a further aspect of the invention.

The treatment of primary or secondary hyperaldosteronism comprising administering a compound of the invention is a further aspect of the invention.

A suitable class of modulators of 5-HT receptors which are subject to the improvements provided by the present invention have a aromatic moiety (Ar), an amide or ester (C(O)—O or C(O)—NH), an optional spacer moiety (G), and the aforementioned basic nitrogen (BN). Accordingly, a suitable object of the invention is the use of compounds of the formula II for the treatment of conditions affected by the modulation of 5-HT receptors, particularly 5-HT4 receptors, wherein Ar—C(O)-E-G-BN are as defined above, and L is a linker moiety comprising at least 2 atoms and L is an acidic moiety such as a carboxylic acid, a sulphonic acid, a sulphoric acid, a phosphonic acid, and a phosphoric acid, or esters of the acidic moiety.

DESCRIPTION OF THE INVENTION

The invention relates to a compound which fulfils the following: i) a binding affinity to a 5-HT receptor with a $pK_i$ of at least 5; ii) comprises at least one basic nitrogen atom; iii) comprises at least one acidic moiety with a pKa of no more than 6.4, or a salt or ester thereof. Without being bound to a particular theory, it is anticipated that the acidic moiety is to be spaced from the acidic nitrogen atom such that the acidic moiety does not interfere with the binding capacity of the nitrogen atom believed to constitute part of the pharmacophore in 5-HT modulators.

The acidic moiety (A) is thus suitably spaced from the basic nitrogen (BN) by at least 2 atoms. Correspondingly, L in compounds of the invention preferably comprises at least 2 atoms.

In a typical embodiment of the present invention, the compounds of the invention further comprise iv) an aromatic or heteroaromatic ring, more typically an aromatic ring. The acidic moiety may be covalently linked to the aromatic or heteroaromatic ring. Without being bound to a particular theory, it is believed that the acidic moiety is to be within a 20 atom space from either the basic nitrogen or the aromatic/heteroaromatic ring. Typically, the basic nitrogen or the aromatic/heteroaromatic ring is less than 16 atoms, such as less than 10, from the acidic moiety.

An acidic moiety is a group that is at least 90% ionic form at physiological pH, more typically at least 95%, even more typically at least 99% of the group is in ionic form. In a preferred embodiment, the acidic moiety has a pKa of no more than 6, more preferably, no more than 5.5, such as no more than 5.4, 5.3, 5.3, 5.2, 5.1, 5.0. In a most preferred form, the compounds of the invention have a pKa of less than 5.0, such as less than 4.5.

The acidic moiety may be in the form of its ester, in its free ion form, or in a salt form. In the embodiment wherein the acidic moiety is in the form of its ester, after hydrolysis of the ester to the acid or to its free ion form is at least 90% ionic form at physiological pH, more typically at least 95%, even more typically at least 99% of the group is in ionic form. It is to be understood that esters of the acidic moiety are characterised in that their hydrolysis consequently result in the presence of the acid in its protonated form or in its free ion form.

Suitable salts include but are not limited to the counter-ion M selected from the group comprising sodium, potassium, calcium, magnesium, aluminium, iron, and zinc ions. The inventor contemplates salts with ammonia and organic nitrogenous bases strong enough to form salts with carboxylic acids. Bases useful for the formation of pharmaceutically acceptable nontoxic base addition salts of the compound of the present invention form a class whose limits are readily understood by those skilled in the art.

In the present context, the term "halogen" includes fluorine, chlorine, bromine and iodine. In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Illustrative examples of "aryl" rings include optionally substituted phenyl, naphthalenyl, phenanthrenyl, anthracenyl, tetralinyl, fluorenyl, indenyl, and indanyl. A preferred aryl group is phenyl. The term "aryl" relates to aromatic, preferably benzenoid groups connected via one of the ring-forming carbon atoms, and optionally carrying one or more substituents selected from halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. As stated, preferred aryl groups are phenyl, and, most suitably, substituted phenyl groups, carrying one or two, same or different, of the substituents listed above.

The term "heterocyclic ring" is intended to mean three-, four-, five-, six-, seven-, and eight-membered rings wherein carbon atoms together with from 1 to 3 heteroatoms constitute said ring. A heterocyclyl may optionally contain one or more unsaturated bonds situated in such a way, however, that an aromatic π-electron system does not arise. The heteroatoms are independently selected from oxygen, sulphur, and nitrogen.

A heterocyclic ring may further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclic rings may optionally also be fused to aryl rings, such that the definition includes bicyclic structures. Preferred such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Illustrative examples of "heterocyclic rings" are the heterocycles tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, thiazoline, thiazolidine, 1,3-oxathiolane. Binding to the heterocycle may be at the position of a heteroatom or via a carbon atom of the heterocycle, or, for benzo-fused derivatives, via a carbon of the benzenoid ring.

Suitable embodiments of the acidic moiety or an ester thereof selected from the group consisting of $C(O)$—$OR^1$, $OP(O)OR^2OR^2$, $P(O)OR^2OR^2$, $SO_2OR^2$, $SO_3H$, $OSO_3H$, and $PO_3H$ wherein $R^1$ and $R^2$ are independently selected from the group consisting of H, M, $C_{1-15}$-alkyl, $C_{3-8}$-cycloalkyl, aryl, and $R^{1,2}$ wherein $R^{1,2}$ is R'—O—C(O)—R", R'—O—C(O)—O—R", R'—C(O)—O—R", wherein R' and R" are independently selected from the group consisting of $C_{1-15}$-alkyl, $C_{3-8}$-cycloalkyl and aryl. Salts of these acid moieties imply that at least one of R1 and $R^2$ is M. M is a counterion as defined above.

A particularly interesting embodiment of the compounds of the invention are esters of the previously described acidic moiety. Typical esters include alkyl esters, substituted alkyl esters, aryl esters, substituted aryl esters and acyloxyalkyl esters. Exemplary embodiments of esters of acidic moieties include

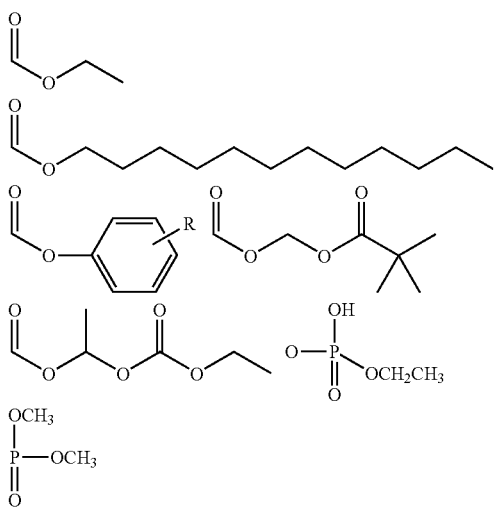

In another suitable embodiment, the compound of the invention has a $pK_i$ of at least 5.5, such as at least 6.

The compounds of the invention may be agonist, antagonists, reverse agonists, partial agonists, or partial antagonists of a 5-HT receptor. Typically, the compound of the invention will have either agonist or partial agonistic activity towards at least one receptor sub-group and optionally concomitant antagonist or partial antagonistic activity toward at least one other receptor sub-group. In a preferred embodiment of the invention, the compounds of the invention have a binding affinity with a $pK_i$ of at least 5, such as at least 5.5, preferably at least 6 to the 5-HT4 or 5-HT3 receptor subgroup.

In a typical embodiment, the compound of the invention has a binding $pK_i$ for a 5-HT receptor of at least 5 and is of the formula I

   BN-L-A   I wherein BN is a basic nitrogen moiety; and
-A is an acidic moiety with a pKa of no more than 6.4 or an ester thereof;
wherein BN-L-A comprises at least 3 consecutive chemical bonds between BN and the acidic moiety.

In a preferred embodiment, L is a linker comprising at least 2 atoms. In the preferred embodiments where the acidic moiety or an ester thereof is selected from the group consisting of $C(O)$—$OR^1$, $OP(O)OR OR^2$, $P(O)OR OR^2$, $SO_2OR^2$, $SO_3H$, $OSO_3H$, and $PO_3H$, the 3 consecutive chemical bonds, typically 4 consecutive chemical bonds, are between the nitrogen atom and C atom of —$C(O)$—$OR^1$, the P atom of —OP(O)$OR^2OR^2$, the P atom of —P(O)$OR^2OR^2$, the P atom of $PO_3H$ and the S atom of —$SO_2OR^2$.

The basic nitrogen moiety may be in the any array of organic forms of nitrogen. Suitable forms of the basic nitrogen moiety may be selected from the group comprising an amine group, amide group, carbamates and urea derivatives, carbazimidamides, a nitrogen-containing heterocyclic or heteroarylic ring, including azabicycles.

Amine groups can be primary, secondary or tertiary amines. Suitable nitrogen-containing heterocyclic or heteroaryl include pyridyl (pyridinyl), pyrimidinyl, thiazolyl, pyrazolyl, imidazolyl, tetrazolyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, .beta.-carbolinyl, phenanthridinyl, acridinyl, perimidinyl, phenanthrolinyl, phenazinyl, phenarsazinyl, phenothiazinyl, furazanyl, phenoxazinyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Preferable heterocyclic groups include piperidino, morpholino, thiamorpholino, pyrrolidino, pyrazolino, pyrazolidino, pyrazoryl, piperazinyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl.

In a typical embodiment of compounds of the formula BN-L-A, the compounds of the invention have the formula II,

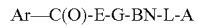   Ar—C(O)-E-G-BN-L-A   II wherein Ar is an monocyclic or polycyclic aromatic or heteroaromatic; C(O) is absent or a carbonyl carbon; and E is absent or selected from the group consisting of O and NH; G is selected from the group consisting of $C_{1-6}$-alkyl, $C_{3-7}$-cycloalkyl, $C_{1-6}$-alkyl-$C_{3-7}$-cycloalkyl, $C_{3-7}$-cycloalkyl-$C_{1-6}$-alkyl; or wherein G-N together form a $C_{3-7}$-heteroalkyl, or a $C_{1-6}$-alkyl-$C_{3-7}$-heteroalkyl.

A highly commercially relevant aspect of the invention is directed to a compound of formula II,

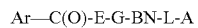   Ar—C(O)-E-G-BN-L-A   II wherein Ar is selected from the group consisting of an optionally substituted aryl ring, an optionally substituted aryl ring fused with one or more non-aromatic optionally substituted carbocylic rings, an optionally substituted aryl ring fused with one or more optionally substituted non-aromatic heterocyclic rings, an optionally substituted aryl ring fused with one or more optionally substituted aromatic or heteroaromatic rings, C(O) is absent or a carbonyl carbon;

E is absent or selected from the group consisting of O and NH;

G is absent or selected from the group consisting of $C_{1-6}$-alkyl, $C_{3-7}$-cycloalkyl, $C_{1-6}$-alkyl-$C_{3-7}$-cycloalkyl, $C_{3-7}$-cycloalkyl-$C_{1-6}$-alkyl;

wherein BN is a basic nitrogen moiety selected from the group consisting of an amine group, an amide group, a carbamate or a carbamate derivative, urea or a urea derivative, a carbazimidamide, a nitrogen-containing heterocyclic, a nitrogen-containing heteroarylic ring, and an azabicyclic ring;

L is absent or selected from the group consisting of straight chain or branched optionally substituted $C_{1-10}$-alkyl, optionally substituted $C_{2-10}$-alkenyl, optionally substituted $C_{2-10}$-alkynyl, $C_{1-10}$-alkylamine, $C_{1-10}$-alkoxy, $C_{2-10}$-alkenyloxy, $C_{2-10}$-alkynyloxy, $C_{1-10}$-alkoxycarbonyl, $C_{2-10}$-alkenyloxycarbonyl, $C_{2-10}$-alkynyloxycarbonyl or combinations thereof; and A is selected from the group consisting of C(O)—OR$^1$, OP(O)OR$^2$OR$^2$, P(O)OR$^2$OR$^2$, SO$_{20}$R$^2$, SO$_3$H, OSO$_3$H, and PO$_3$H; wherein R$^1$ and R$^2$ are independently selected from the group consisting of H, M, $C_{1-15}$-alkyl, $C_{3-8}$-cycloalkyl, aryl, and R$^{1,2}$ wherein R$^{1,2}$ is R'—O—C(O)—R", R'—O—C(O)—O—R", R'—C(O)—O—R", wherein R' and R" are independently selected from the group consisting of $C_{1-15}$-alkyl, $C_{3-8}$-cycloalkyl and aryl.

Suitably, the basic nitrogen moiety may be selected from the group consisting of pyridyl (pyridinyl), pyrimidinyl, thiazolyl, pyrazolyl, imidazolyl, tetrazolyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, .beta.-carbolinyl, phenanthridinyl, acridinyl, perimidinyl, phenanthrolinyl, phenazinyl, phenarsazinyl, phenothiazinyl, furazanyl, phenoxazinyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Preferable heterocyclic groups include piperidino, morpholino, thiamorpholino, pyrrolidino, pyrazolino, pyrazolidino, pyrazoryl, piperazinyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl, each of which may be optional substituted.

In a most preferred embodiment of the compounds of the invention, the basic nitrogen moiety is selected from the group consisting of carbazimidamide and optional substituted piperidinyl.

In terms of the aryl moiety, Ar may be suitably selected from optionally substituted benzyl, naphthalene, indoline, indole, oxazinoindoline, indolizine, isoindoline, indene, indane, indazole, azulene, benzimidazole, benzofuran, benzothiophene, benzthiazole, purine, 4H-quinolizine, quinoline, isoquinoline, cinnoline, phthalazine, quinazoline, quinoxaline, 1,3-naphthyridine, pteridine, coumaran, benzodioxane, benzopyran, chroman, isochroman, carbazole, acridine, phenazine, phenothiazine, phenoxazine, thianthrene, phenanthrene, anthracene, tetraline, fluorene, and acenaphthylene, each of which may be optionally substituted.

The inventors have demonstrated in the enclosed examples the general applicability of the term Ar by demonstrating at least the suitability of embodiments wherein Ar is selected from benzyl, naphthalene, indole, benzodioxane, indazole, and oxazinoindole.

Typically, in embodiments wherein Ar is a bi- or polycyclic system, the bond between Ar and the C(O), G or the basic nitrogen moiety stems from the atom of Ar neighbouring the atoms shared by the fused bicyclic system.

As can be seen from the Examples, in typical embodiments, L may be absent or selected from the group consisting of optionally substituted $Cl_{1-10}$-alkyl, $C_{1-10}$-alkylamine, $C_{1-10}$-alkoxy, and $C_{1-10}$-alkoxycarbonyl.

L is typically selected from straight chain or branched optionally substituted $C_{1-10}$-alkyl, $C_{1-10}$-alkylamine or $C_{1-10}$-alkoxy. In embodiments wherein L is a branched chain optionally substituted $C_{1-10}$-alkyl, $C_{1-10}$-alkylamine or $C_{1-10}$-alkoxy, there may be one or two acidic moieties A, namely L-A may be of the formula

where X is selected from the group consisting of C and N and i, j, and k are independently selected from a whole number selected from the group consisting of 0-10 (wherein the sum i+j+k is typically less than 10; and one or both of the A groups is as defined above, the other being absent. An exemplary embodiment of branched optionally substituted $C_{1-10}$-alkyl, $C_{1-10}$-alkylamine or $C_{1-10}$-alkoxy is The Examples demonstrate the great suitability of embodiments wherein A is selected from the group consisting of —C(O)—OR$^1$, and —P(O)OR$^2$OR$^2$, wherein R$^1$ and R$^2$ are independently selected from the group consisting of H, M, $C_{1-15}$-alkyl, $C_{3-8}$-cycloalkyl, and aryl. Particularly interesting are the carboxylic acids or their alkyl esters, such as their trichloroethyl esters.

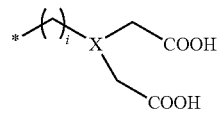

Typically, G is absent or selected from the group consisting of $C_{1-6}$-alkyl, preferably absent or $C_{1-3}$-alkyl.

In a combination of preferred embodiments, as can be seen from the examples, compounds wherein L is absent or selected from the group consisting of optionally substituted $C_{1-8}$-alkyl and wherein A is selected from the group consisting of —C(O)—OR$^1$, and —P(O)OR$^2$OR$^2$, wherein R$^1$ and R$^2$ are independently selected from the group consisting of H and $C_{1-15}$-alkyl are highly relevant.

In a further combination of interesting embodiments, G is absent or $C_{1-3}$-alkyl; the basic nitrogen moiety is selected from the group consisting of carbazimidamide and optional substituted piperidinyl; and L is absent or selected from the group consisting of optionally substituted $C_{1-8}$-alkyl.

A further aspect of the invention is directed to the use of a compound of formula II as defined supra, or a composition comprising said compound or a salt of said compound for the preparation of a medicament for the treatment of a cardiovascular disorder. The cardiovascular disorder is typically selected from the group consisting of tachycardia, bradycardia, cardioexcitation, cardiodepression, arrhythmia, fibrillation, atrial fibrillation, Paroxysmal Supraventricular Tachycardia (PSVT), thromoembolisms and VTE.

A related aspect of the invention is directed to the use of a compound of formula II as defined herein, or a composition comprising said compound or a salt of said compound for the preparation of a medicament for the treatment of a gastrointestinal disorder or lower urinary tract disorder. The gastrointestinal disorder may be selected from the group consisting of irritable bowel syndrome; gastrointestinal hypomotility disorders; gastro-esophageal reflux, such as heartburn or mild oesophagitis; functional or nonulcer dyspensia; gastroparesis; nausea and vomiting; early satiety in the elderly; paraneoplastic of HIV-associated gastroparesis; drug-induced delays in gastric emptying and functional bowel obstructions, such as bowel obstructions caused by pancreatic cancer or drugs; and emesis. An related aspect of the invention relates to the use of the compounds of the invention for the preparation of a medicament for the prophylaxis or treatment of gastrointestinal disorders suitable and for symptoms of Irritable Bowel Syndrome, including abdominal pain and disrupted colonic motility; diarrhea; constipation; urinary incontinence and anal incontinence.

WO 96/10027, in the preparation of compounds for use in the treatment of conditions involving a decreased motility of the intestine, prepared the 4-aminobenzofuran carboxylates

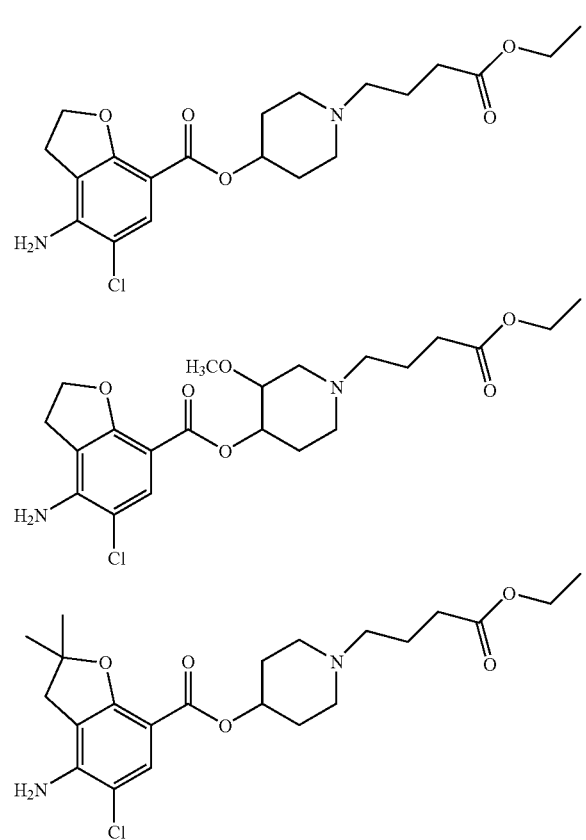

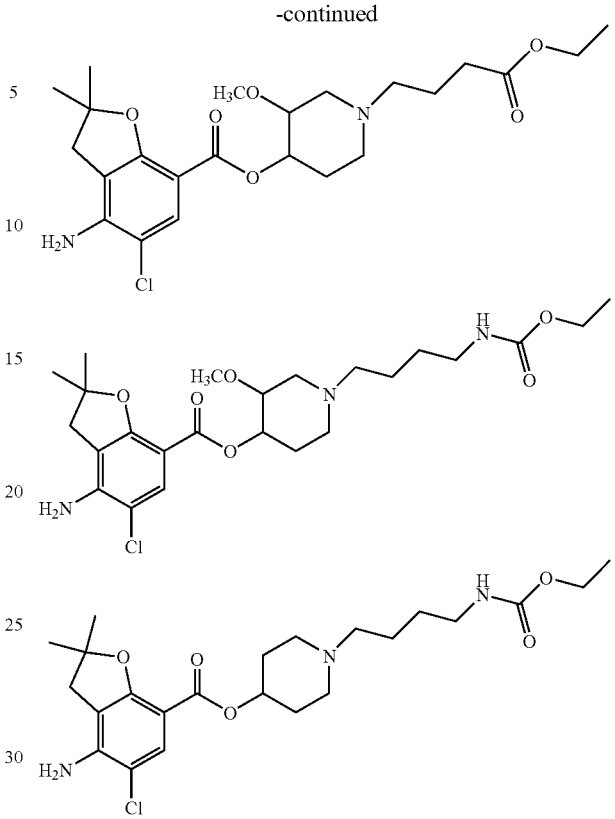

which, in a suitable embodiment of the present invention, are disclaimed only as such and in the context of their use for the preparation of a medicament for use in the treatment of conditions involving a decreased motility of the intestine.

In an alternative embodiment of the compounds invention as such and in the context of their use for the preparation of a medicament for use in the treatment of conditions involving a decreased motility of the intestine, Ar—C(O)-E is not a 4-aminobenzofuran, not a 4-aminocoumaran, and not a 4-aminochroman carboxylate The 4-position is to be understood as para to carboxylate.

In a further alternative embodiment of the compounds of the present invention as such and in the context of their use for the preparation of a medicament for use in the treatment of conditions involving a decreased motility of the intestine, Ar is not a 4-aminobenzofuran, not a 4-aminocoumaran, and not a 4-aminochroman—the 4-position being para to the remainder amide or carboxylate in Ar—C(O)-E-G-BN-L-A. WO 01/93849 in the preparation of compounds for the treatment of gastroesophageal reflux disease disclosed benzamide derivatives. In an alternative embodiment of the compounds invention as such and in the context of compounds for the treatment of gastroesophageal reflux disease, when Ar is a phenyl thrice substituted with $NH_2$, Cl, and/or $CH_3$, A is a carboxylic acid or ester, L is not an optionally substituted $C_{2-8}$-alkyl, $C_{2-8}$-alkoxy, $C_{2-8}$-alkenyloxy, $C_{2-8}$-alkynyloxy, $C_{2-8}$-alkoxycarbonyl, $C_{2-8}$-alkenyloxycarbonyl or $C_{2-8}$-alkynyloxycarbonyl.

The inventors further disclaim, as such, and in the context of the context of improving gastrointestinal tract motility, compounds of the formula

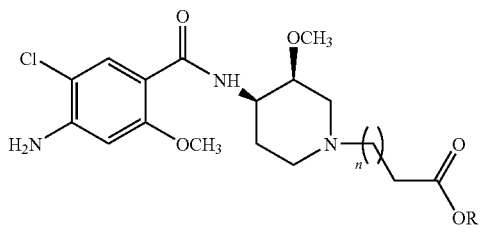

wherein R is selected from H, methyl, ethyl, isopropyl, sec-butyl, and 4-fluorophenyl and n is 0, 1, 2, 3, or 4. More typically, the inventors herein disclaim compounds, as such, wherein n is from 0 to 8 and R is hydrogen, lower alkyl, or substituted aryl.

Generally stated, the invention relates to method of treating a disease associated, at least in part, with peripheral 5HT receptor comprising administering a compound of formula I, II, III, IV, V, or VI. Accordingly, one aspect of the invention is directed to a method of treating a cardiovascular disorder comprising administering a compound of formula I, II, III, IV, V, or VI. Similarly, a further aspect relates to method of treating gastrointestinal disorders comprising administering a compound of the invention. A still further aspect of the invention is directed a method of treating lower urinary tract disorders comprising administering a compound of the invention.

Most typically, the compounds of the invention act and are intended to act on the 5-HT$_4$ receptor subgroup.

In a typical embodiment of compounds of the formula BN-L-A, the compounds of the invention have the formula II, Ar—C(O)-E-G-BN-L-A, wherein Ar is an aromatic or heteroaromatic, including fused aromatic systems; E is absent or selected from the group consisting of O and NH; G is selected from the group consisting of $C_{1-6}$-alkyl, $C_{3-7}$-cycloalkyl, $C_{1-6}$-alkyl-$C_{3-7}$-cycloalkyl, $C_{3-7}$-cycloalkyl-$C_{1-6}$-alkyl; or wherein G-BN together form a $C_{3-7}$-heteroalkyl, or a $C_{1-6}$-alkyl-$C_{3-7}$-heteroalkyl; and L-A is selected from the group consisting of $C_{2-6}$-alkyl-C(O)—OR$^1$, $C_{2-6}$-alkyl-OP(O)OR$^2$OR$^2$, $C_{2-6}$-alkyl-P(O)OR$^2$OR$^2$, $C_{2-6}$-alkyl-SO$_2$OR$^2$, $C_{2-6}$-alkyl-PO$_3$H, $C_{3-7}$-cycloalkyl-C(O)—OR$^1$, $C_{3-7}$-cycloalkyl-OP(O)OR$^2$OR$^2$, $C_{3-7}$-cycloalkyl-P(O)OR$^2$OR$^2$, $C_{3-7}$-cycloalkyl-SO$_2$OR$^2$, $C_{3-7}$-cycloalkyl-PO$_3$H, ($C_{1-6}$-alkyl)aryl-C(O)—OR$^1$, ($C_{1-6}$-alkyl)aryl-OP(O)OR$^2$OR$^2$, ($C_{1-6}$-alkyl)aryl-P(O)OR$^2$OR$^2$, ($C_{1-6}$-alkyl)aryl-SO$_2$OR$^2$, ($C_{1-6}$-alkyl)aryl-PO$_3$H, aryl-C(O)—OR$^1$, aryl-OP(O)OR$^2$OR$^2$, aryl-P(O)OR$^2$OR$^2$, aryl-SO$_2$OR$^2$ and aryl-PO$_3$H.

Exemplary embodiments of compounds of the formula II include compounds of formula III as well compounds of the formula IIa-f, wherein, in IIa-d, the Ar—C(O) moiety is fused into a bicyclic or tricyclic system. Thus, an alternate embodiment of compounds of formula II-ii is of the formula (Ar—C(O))-E-G-BN-L-A      II-ii to illustrate that the carbonyl is within the monocyclic or polycyclic aromatic or heteroaromatic.

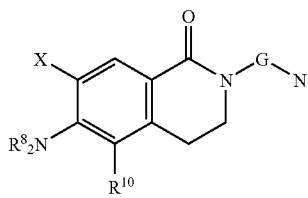

II-a

-continued

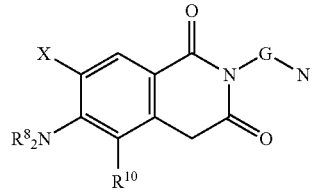

II-b

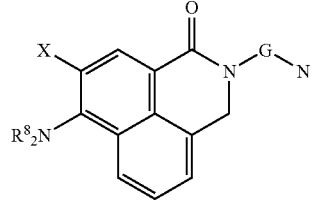

II-c

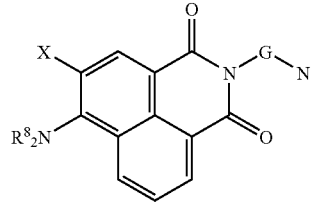

II-d

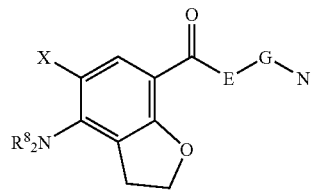

II-e

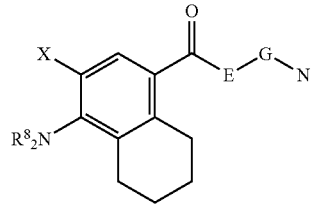

II-f

A still further embodiment of the invention comprises compounds of the formula II-iii, Ar—C(O)-G-BN-L-A      II-iii wherein Ar—C(O) is an arylketone, such as an amino arylketone. Exemplary aryl ketones include benzodioxanyl ketones.

Suitable embodiments of compounds of formula II, A-C(O)-E-G-BN-L-A, and IV include embodiments where A-C(O)-E is selected from the group comprising of optionally substituted indole esters, isoindole esters, indoline esters, indazole esters, benzimidiazole esters, benzthiazole esters, purine estes, quinoline esters, isoquinoline esters, cinnoline esters, carbazole esters and acridine esters.

An exemplary embodiment of compounds of formula II include naphthalimides derivatized with a basic nitrogen and an acidic moiety.

A and A-C(O) may be selected from any array of aromatic, heteroaromatic or fused aromatic systems. Formulas II-e and II-f are exemplary embodiments of compounds of formula III wherein R$^9$ and R$^{10}$ form a ring system.

In a suitable embodiment of compounds of formula II, A-C(O)-E-G-BN-L-A, the G-BN moiety forms a heterocyclic ring, such as exemplified in compounds IIIa-d.

In a suitable embodiment of a compound of the of the formula I or II is a compound of the formula III

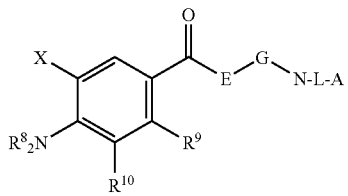

III wherein L-A is selected from the group consisting of $C_{2-6}$-alkyl-C(O)—$OR^1$, $C_{2-6}$-alkyl-OP(O)$OR^2OR^2$, $C_{2-6}$-alkyl-P(O)$OR^2OR^2$, $C_{2-6}$-alkyl-SO$_2OR^2$, $C_{2-6}$-alkyl-PO$_3$H, $C_{3-7}$-cycloalkyl-C(O)—$OR^1$, $C_{3-7}$-cycloalkyl-OP(O)$OR^2OR^2$, $C_{3-7}$-cycloalkyl-P(O)$OR^2OR^2$, $C_{3-7}$-cycloalkyl-SO$_2OR^2$, $C_{3-7}$-cycloalkyl-PO$_3$H, ($C_{1-6}$-alkyl)aryl-C(O)—$OR^1$, ($C_{1-6}$-alkyl)aryl-OP(O)$OR^2OR^2$, ($C_{1-6}$-alkyl)aryl-P(O)$OR^2OR^2$, ($C_{1-6}$-alkyl)aryl-SO$_2OR^2$, ($C_{1-6}$-alkyl)aryl-PO$_3$H, aryl-C(O)—$OR^1$, aryl-OP(O)$OR^2OR^2$, aryl-P(O)$OR^2OR^2$, aryl-SO$_2OR^2$ and aryl-PO$_3$H; and E is selected from the group consisting of O and NH; G is selected from the group consisting of $C_{1-6}$-alkyl, $C_{3-7}$-cycloalkyl, $C_{1-6}$-alkyl-$C_{3-7}$-cycloalkyl, $C_{3-7}$-cycloalkyl-$C_{1-6}$-alkyl; or wherein G-N together form a $C_{3-7}$-heteroalkyl, or a $C_{1-6}$-alkyl-$C_{3-7}$-heteroalkyl; X is a halogen; $R^8$ is independently selected from H and $C_{1-6}$-alkyl; $R^9$ and $R^{10}$ are independently selected from the group consisting of H, O—$C_{1-6}$-alkyl, $C_{1-6}$-alkyl, a $C_{3-7}$-cycloalkyl, a heterocycloalkyl, a heteroaryl, or an aryl; or wherein together $R^9$ and $R^{10}$ form a $C_{3-7}$-cycloalkyl, a heterocycloalkyl, a heteroaryl, or an aryl; or wherein $NR^8_2$ and $R^{10}$ together form a heterocycloalkyl.

Compounds of the formula III may be, for instance, amino benzamide derivatives or amino benzoates.

In a particularly interesting embodiment compounds of formula II, A is selected from the group consisting of optionally substituted benzyl, imidazopyridine, indole, isoindole, indoline, indazole and benzimidazole.

Depending on the position of the basic nitrogen group, L may be absent altogether and the acidic moiety may be directly linked to a compound with 5-HT activity. An exemplary embodiment is compound III-e but also compound III-d which can be seen as, in the embodiment wherein L is a butyl chain, the acidic modification of SB 204070 directly onto the alkyl chain.

In a typical embodiments of compounds of formula III, $R^{10}$ is H and $R^9$ is O—$C_{1-6}$-alkyl.

In another typical embodiment of compounds of formula III, $R^9$ and $R^{10}$ form a heterocyclic ring selected from the group consisting of 1,4-dioxane, 1,3-dioxolane, pyridine, thiadiazole, pyrrolidine, pyrroline, pyrrole, furan and piperidine.

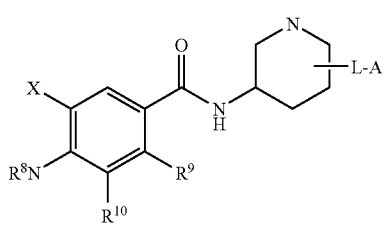

III-a

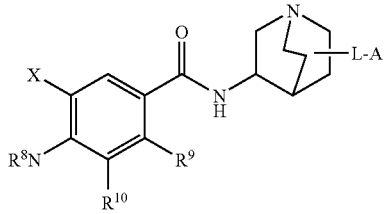

III-b

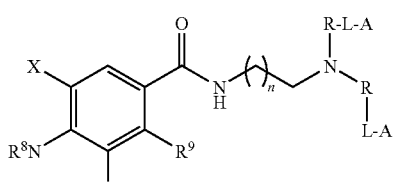

III-c

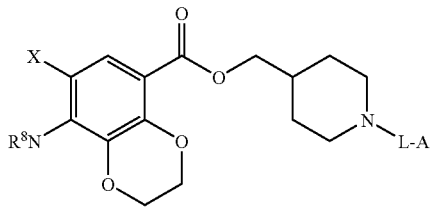

III-d

Exemplary embodiments of this aspect of the invention include dihydrobenzofurans.

In an exemplary embodiment of III-c, n is 1, X is Cl, $R^8$ are H, $R^9$ is OMe, $R^{10}$ is H and R are each ethyl. Thus, the embodiment is a derivative of metoclopamide wherein the terminal ethylene groups of the tertiary ethylamine are modified with an acidic moiety. This exemplary embodiment is a demonstrating of the possibility of L being absent. In an alternate embodiment, only one of the ethylene moieties are modified with an acidic moiety.

In a further exemplary embodiment, the invention defines embodiments wherein Zacopride is modified with an acidic moiety (III-b). In an interesting embodiment is of III-b, the acidic moiety is bound directly to Zacopride, such as in III-e III-e

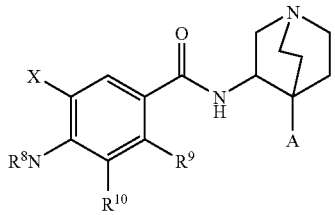

III-e

A particularly interesting embodiment of compounds of formula III includes cisapride and norcisapride, including optically active forms thereof, each modified with an acidic moiety. Preferably, when the acidic moiety is a carboxylic acid or ester attached to the piperidinyl ring of cisapride or norcisapride, is preferably not attached to the piperidinyl nitrogen but rather to a carbon on the piperidinyl ring.

In a further interesting embodiment, in a compound of the of the formula I or II, BN has the formula IV,

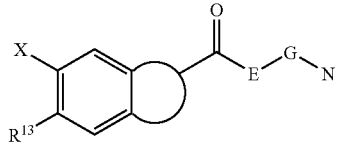
IV and L-A is selected from the group consisting of $C_{2-6}$-alkyl-C(O)—$OR^1$, $C_{2-6}$-alkyl-OP(O)$OR^2OR^2$, $C_{2-6}$-alkyl-P(O)OR $OR^2$, $C_{2-6}$-alkyl-SO$_2OR^2$, $C_{2-6}$-alkyl-PO$_3$H, $C_{3-7}$-cycloalkyl-C(O)—$OR^1$, $C_{3-7}$-cycloalkyl-OP(O)$OR^2OR^2$, $C_{3-7}$-cycloalkyl-P(O)$OR^2OR^2$, $C_{3-7}$-cycloalkyl-SO$_2OR^2$, $C_{3-7}$-cycloalkyl-PO$_3$H, ($C_{1-6}$-alkyl)aryl-C(O)—$OR^1$, ($C_{1-6}$-alkyl)aryl-OP(O)$OR^2OR^2$, ($C_{1-6}$-alkyl)aryl-P(O)$OR^2OR^2$, ($C_{1-6}$-alkyl)aryl-SO$_2OR^2$, ($C_{1-6}$-alkyl)aryl-PO$_3$H, aryl-C(O)—$OR^1$, aryl-OP(O)$OR^2OR^2$, aryl-P(O)$OR^2OR^2$, aryl-SO$_2OR^2$ and aryl-PO$_3$H;

E is selected from the group consisting of O and NH;

G is selected from the group consisting of $C_{1-6}$-alkyl, $C_{3-7}$-cycloalkyl, $C_{1-6}$-alkyl-$C_{3-7}$-cycloalkyl, $C_{3-7}$-cycloalkyl-$C_{1-6}$-alkyl; or wherein G-N together form a $C_{3-7}$-heteroalkyl, or a $C_{1-6}$-alkyl-$C_{3-7}$-heteroalkyl;

and wherein the

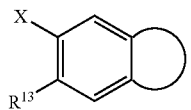

moiety is selected from the group consisting of an oxazinoindole,

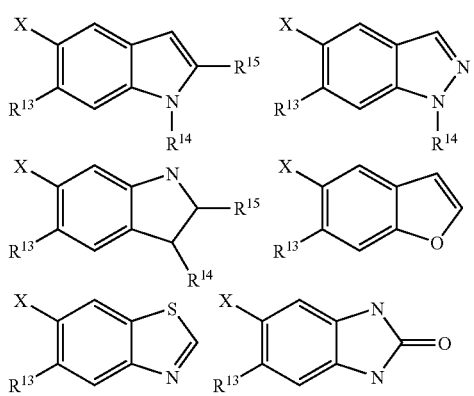

wherein X is absent or a halogen;
$R^{13}$ is selected from the group consisting of H, NH$_2$, and $C_{1-6}$-alkyl; and
$R^{14}$ and $R^{15}$ are independently selected from the group consisting of H, and $C_{1-6}$-alkyl; or wherein $R^{14}$ and $R^{15}$ together from a $C_{3-7}$-cycloalkyl or a $C_{3-7}$-heterocycle. Suitably, R14 and R15 form a tetrahydropyran.

In a preferred embodiment wherein of compounds of formula IV, the ester is covalently linked to the heterocycle. In a most preferred embodiment, the ester is covalently linked to the α-carbon or other α-atom, such as the heteroatom α-situated from the aryl ring.

Exemplary embodiments of compounds of formula IV include indole and indoline esters and amides of the formula IVa-d.

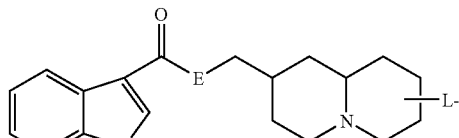
IV-a

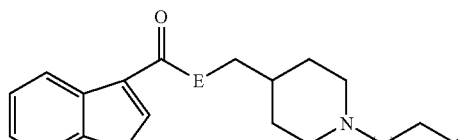
IV-b

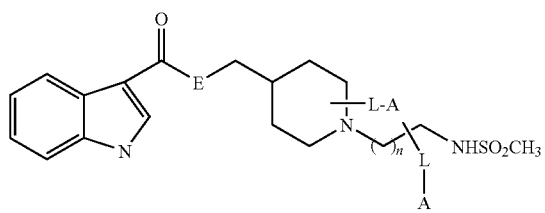
IV-c

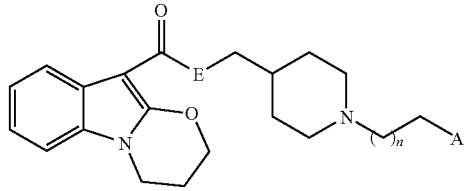
IV-d wherein n is an whole number selected from 0-10, such as 1, 2, 3, 4, 5, 6, 7 8, 9, and 10.

As stated, in a most preferred embodiment of compounds of formula II, Ar is selected from the group consisting of phenyl naphthalene, indole, benzodioxane, indazole, and oxazinoindole. The present inventors have found compounds of formula II comprising an oxazinoindole to be rather interesting, such as compound IV-d.

In a particularly interesting embodiment, the compound of formula II is a derivative of piboserod, namely of the formula IV-P

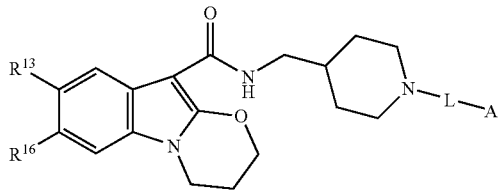
IV-P wherein L is absent or selected from the group consisting of straight chain or branched optionally substituted $C_{1-10}$-alkyl, optionally substituted $C_{2-10}$-alkenyl, optionally substituted $C_{2-10}$-alkynyl, $C_{1-10}$-alkylamine, $C_{1-10}$-alkoxy, $C_{2-10}$-alkenyloxy, $C_{2-10}$-alkynyloxy, $C_{1-10}$-alkoxycarbonyl, $C_{2-10}$-alkenyloxycarbonyl, $C_{2-10}$-alkynyloxycarbonyl or combinations thereof; and A is selected from the group consisting of $C(O)-OR^1$, $OP(O)OR^2OR^2$, $P(O)OR^2OR^2$, $SO_2OR^2$, $SO_3H$, $OSO_3H$, and $PO_3H$; wherein $R^1$ and $R^2$ are independently selected from the group consisting of H, M, $C_{1-15}$-alkyl, $C_{3-8}$-cycloalkyl, aryl, and $R^{1,2}$ wherein $R^{1,2}$ is R'—O—C(O)—R", R'—O—C(O)—O—R", R'—C(O)—O—R", wherein R' and R" are independently selected from the group consisting of $C_{1-15}$-alkyl, $C_{3-8}$-cycloalkyl and aryl;

$R^{13}$ is selected from the group consisting of H, halogen, $NH_2$, and $C_{1-6}$-alkyl; and $R^{16}$ is selected from the group consisting of H, halogen, OH, O—$C_{1-6}$-alkyl, and $C_{1-6}$-alkyl.

L is typically selected from straight chain or branched optionally substituted $C_{1-10}$-alkyl, $C_{1-10}$-alkoxycarbonyl, $C_{1-10}$-alkylamine or $C_{1-10}$-alkoxy. In embodiments wherein L is a branched chain optionally substituted $C_{1-10}$-alkyl, $C_{1-10}$-alkylamine or $C_{1-10}$-alkoxy, there may be one or two acidic moieties A, namely L-A may be of the formula

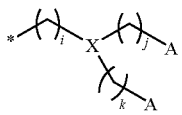

where X is selected from the group consisting of C and N and i, j, and k are independently selected from a whole number selected from the group consisting of 0-10, wherein the sum i+j+k is typically less than 10; and one or both of the A groups is as defined above, the other being absent.

An exemplary embodiment of branched optionally substituted $C_{1-10}$-alkyl, $C_{1-10}$-alkoxycarbonyl, $C_{1-10}$-alkylamine or $C_{1-10}$-alkoxy is

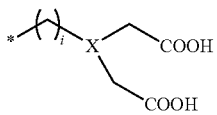

In a most preferred embodiment of compounds of the formula IV-P, L-A is selected from the group consisting of a straight chain $C_{1-10}$-alkyl-$CO_2H$, a straight chain $C_{1-10}$-alkyl-$C(O)$—$OR^1$, a branched $C_{1-10}$-alkyl-$CO_2H$, a branched $C_{1-10}$-alkyl-$C(O)$—$OR^1$ and di($C_{1-10}$-alkoxycarbonyl)s of the formula $C_{1-10}$-alkyl-C(O)O—CH($C_{1-10}$-alkyl)-OC(O)O—$C_{1-10}$-alkyl, $C_{1-10}$-alkyl-C(O)O—CH($C_{1-10}$-alkyl)-C(O)O—$C_{1-10}$-alkyl, and $C_{1-10}$-alkyl-C(O)O—CH($C_{1-10}$-alkyl)-OC(O)—$C_{1-10}$-alkyl.

A further interesting embodiment of compounds having i) a binding affinity to a 5-HT receptor with a $pK_i$ of at least 5; ii) comprises at least one basic nitrogen atom; iii) comprises at least one acidic moiety with a pKa of no more than 6.4, or a salt or ester thereof; and iv) an aromatic or heteroaromatic ring, more typically an aromatic ring is a compound of formula V

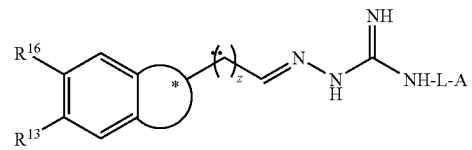

wherein L-A is selected from the group consisting of $C_{2-6}$-alkyl-C(O)—$OR^1$, $C_{2-6}$-alkyl-OP(O)$OR^2OR^2$, $C_{2-6}$-alkyl-P(O)$OR^2OR^2$, $C_{2-6}$-alkyl-$SO_2OR^2$, $C_{2-6}$-alkyl-$PO_3H$, $C_{3-7}$-cycloalkyl-C(O)—$OR^1$, $C_{3-7}$-cycloalkyl-OP(O)$OR^2OR^2$, $C_{3-7}$-cycloalkyl-P(O)$OR^2OR^2$, $C_{3-7}$-cycloalkyl-$SO_2OR^2$, $C_{3-7}$-cycloalkyl-$PO_3H$, ($C_{1-6}$-alkyl)aryl-C(O)—$OR^1$, ($C_{1-6}$-alkyl)aryl-OP(O)$OR^2R^2$, ($C_{1-6}$-alkyl)aryl-P(O)$OR^2OR^2$, ($C_{1-6}$-alkyl)aryl-$SO_2OR^2$, ($C_{1-6}$-alkyl)aryl-$PO_3H$, aryl-C(O)—$OR^1$, aryl-OP(O)$OR^2OR^2$, aryl-P(O)$OR^2OR^2$, aryl-$SO_2OR^2$ and aryl-$PO_3H$; Z is an integer selected from the group consisting of 0, 1, and 2, and wherein the aromatic bicyclic ring

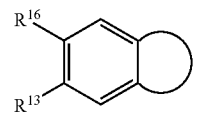

moiety is selected from the group consisting of

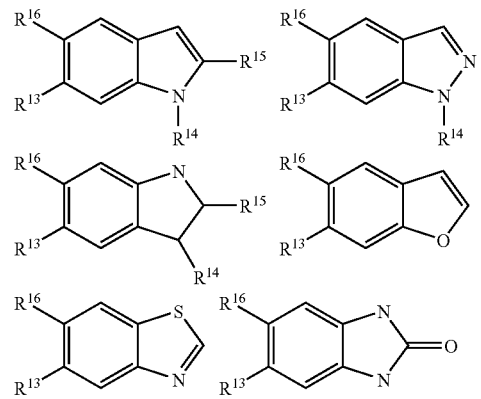

wherein $R^{13}$ is selected from the group consisting of H, $NH_2$, and $C_{1-6}$-alkyl;

$R^{14}$ and $R^{15}$ are independently selected from the group consisting of H, and $C_{1-6}$-alkyl; or $R^{14}$ and $R^{15}$ together from a $C_{3-7}$-cycloalkyl or a $C_{3-7}$-heterocycle; and $R^{16}$ is selected from the group consisting of H, OH, O—$C_{1-6}$-alkyl, and $C_{1-6}$-alkyl.

Compounds of formula V will be recognised by the skilled artisan as derivatives of compounds of the formula II, namely the aryl ketones of formula II-iii, A-C(O)-G-BN-L-A.

Further interesting embodiments of the aromatic bicyclic ring may be selected from the group comprising indene, naphthalene, coumaran, benzofuran, azulene, indole, isoindole, indoline, indazole, benzimidiazole, benzthiazole, purine, quinoline, isoquinoline, cinnoline, carbazole, and acridine.

An exemplary embodiment of compounds of the formula V include compound V-a

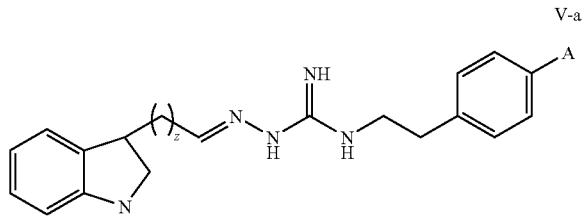

V-a

A particularly interesting embodiment of the invention relates to derivatives of tegaserod

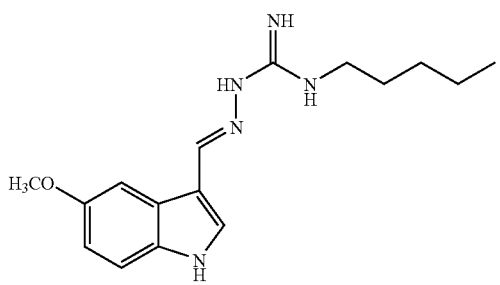

wherein the aliphatic chain is derivatized to comprise an acidic moiety and optional modification of the bicyclic aromatic. An interesting embodiment of the invention is a compound of formula VI,

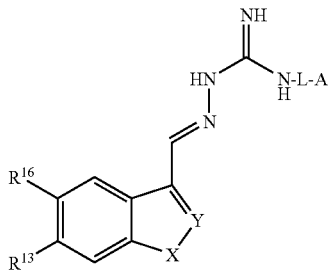

VI wherein X and Y are independently selected from the group consisting of NH, O, C, and S;

L is absent or selected from the group consisting of straight chain or branched optionally substituted $C_{1-10}$-alkyl, optionally substituted $C_{2-10}$-alkenyl, optionally substituted $C_{2-10}$-alkynyl, $C_{1-10}$-alkylamine, $C_{1-10}$-alkoxy, $C_{2-10}$-alkenyloxy, $C_{2-10}$-alkynyloxy, $C_{1-10}$-alkoxycarbonyl, $C_{2-10}$-alkenyloxycarbonyl, $C_{2-10}$-alkynyloxycarbonyl or combinations thereof;

A is selected from the group consisting of $C(O)$—$OR^1$, $OP(O)OR^2OR^2$, $P(O)OR^2OR^2$, $SO_2OR^2$, $SO_3H$, $OSO_3H$, and $PO_3H$; wherein $R^1$ and $R^2$ are independently selected from the group consisting of H, M, $C_{1-15}$-alkyl, $C_{3-8}$-cycloalkyl, aryl, and $R^{1,2}$ wherein $R^{1,2}$ is R'—O—C(O)—R", R'—O—C(O)—O—R", R'—C(O)—O—R", wherein R' and R" are independently selected from the group consisting of $C_{1-15}$-alkyl, $C_{3-8}$-cycloalkyl and aryl;

and $R^{16}$ and $R^{13}$ are independently selected from the group consisting of H, OH, halogen, $NH_2$, O—$C_{1-6}$-alkyl, and $C_{1-6}$-alkyl.

L is suitably selected from straight chain or branched optionally substituted $C_{1-10}$-alkyl, $C_{1-10}$-alkoxycarbonyl, $C_{1-10}$-alkylamine or $C_{1-10}$-alkoxy. In embodiments wherein L is a branched chain optionally substituted $C_{1-10}$-alkyl, $C_{1-10}$-alkylamine or $C_{1-10}$-alkoxy, there may be one or two acidic moieties A, namely L-A may be of the formula

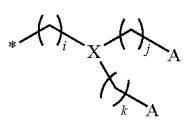

where X is selected from the group consisting of C and N and i, j, and k are independently selected from a whole number selected from the group consisting of 0-10 (wherein the sum i+j+k is typically less than 10; and one or both of the A groups is as defined above, the other being absent. An exemplary embodiment of branched optionally substituted $C_{1-10}$-alkyl, $C_{1-10}$-alkylamine or $C_{1-10}$-alkoxy is

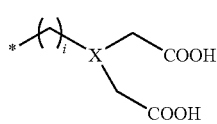

In a highly suitable embodiment, L is a straight chain or branched optionally substituted $C_{1-10}$-alkyl.

Preferably, A is selected from the group consisting of —C(O)—$OR^1$, and —P(O)$OR^2OR^2$, wherein $R^1$ and $R^2$ are independently selected from the group consisting of H, M, $C_{1-15}$-alkyl, $C_{3-8}$-cycloalkyl, and aryl. Particularly interesting are the carboxylic acids or their $C_{1-6}$-alkyl esters, such as their methyl esters, ethyl esters, and trichloroethyl esters In a preferred embodiment of compounds of formula VI, $R^{16}$ is selected from the group consisting of H, OH, O—$C_{1-6}$-alkyl, and $C_{1-6}$-alkyl; and $R^{13}$ is selected from the group consisting of H, $NH_2$, and $C_{1-6}$-alkyl. More preferably, $R^{16}$ is O—$C_{1-6}$-alkyl, most preferably O—$CH_3$.

As stated, the compounds of the invention are 5-HT modulators, typically 5-HT4 modulators. In a suitable embodiment, the compounds of the invention are 5-HT4 agonists. In a further suitable embodiment, the compounds of the invention are 5-HT4 antagonists. In a still further suitable embodiment of the invention, the compounds of the invention are partial agonists.

The subject invention provides novel compounds and compositions for the safe and effective treatment of gastroesophageal reflux and related conditions. These compositions possess potent activity in treating gastroesophageal reflux disease and substantially reduce adverse effects associated with the administration of 5-HT modulators. These adverse effects include, but are not limited to, diarrhea, abdominal cramping and elevations of blood pressure and heart rate.

The compounds of the invention are anticipated are intended for treatment of dyspepsia, gastroparesis, constipation, post-operative ileus, and intestinal pseudo-obstruction. Dyspepsia is a condition characterized by an impairment of the power or function of digestion that can arise as a symptom of a primary gastrointestinal dysfunction or as a complication due to other disorders such as appendicitis, gallbladder disturbances, or malnutrition. Gastroparesis is a paralysis of the stomach brought about by a motor abnormality in the stomach or as a complication of diseases such as diabetes, progressive systemic sclerosis, anorexia nervosa or myotonic dystrophy. Constipation is a condition characterized by infrequent or difficult evacuation of feces resulting from conditions such as lack of intestinal muscle tone or intestinal spasticity. Post-operative ileus is an obstruction in the intestine due to a disruption in muscle tone following surgery. Intestinal pseudo-obstruction is a condition characterized by constipation, colicky pain, and vomiting, but without evidence of physical obstruction.

An important aspect of the invention relates to a method of treating a cardiovascular disorder comprising administering a compound having a binding affinity to a 5-HT receptor with a $pK_i$ of at least 5; ii) comprises at least one basic nitrogen atom; iii) comprises at least one acidic moiety with a pKa of no more than 6.4, or a salt or ester thereof. This method treating a cardiovascular disorder is done essentially free of CNS-related side effects. Typically, the compound having a binding $pK_i$ for a 5-HT receptor of at least 5, said compound comprising a molecular skeleton of the formula I

BN-L-A wherein BN is a basic nitrogen moiety; and -A is an acidic moiety with a pKa of no more than 6.4 or an ester thereof; wherein BN-L-A comprises at least 3 consecutive chemical bonds between BN and the acidic moiety.

In an exemplary embodiment of treating a cardiovascular disorder, the disorder is selected from the group consisting of tachycardia, bradycardia, cardioexcitation, cardiodepression, arrhythmia, fibrillation, atrial fibrillation, Paroxysmal Supraventricular Tachycardia (PSVT), thromoembolisms and VTE.

A further aspect of the invention relates to a method of treating gastrointestinal disorders comprising administering a compound of the invention. In exemplary embodiments of this aspect of the invention, the gastrointestinal disorder is selected from the group consisting of irritable bowel syndrome, gastrointestinal hypomotility disorders such as gastro-esophageal reflux (heartburn, mild oesophagitis); functional or nonulcer dyspensia; gastroparesis, nausea and vomiting; early satiety in the elderly; paraneoplastic of HIV-associated gastroparesis; drug-induced delays in gastric emptying and functional bowel obstructions, such as bowel obstructions caused by pancreatic cancer or drugs; and emesis.

A further aspect of the present invention includes a method of treating a condition caused by gastrointestinal motility dysfunction in a mammal which comprises administering to a mammal in need of treatment for gastrointestinal motility dysfunction, a therapeutically effective amount of a compound of the invention or a pharmaceutically compositions thereof. Conditions caused by gastrointestinal motility dysfunction include, but are not limited to, dyspepsia, gastroparesis, constipation, post-operative ileus, and intestinal pseudo-obstruction. Preferably, the mammal is a human.

In the treatment of treating gastrointestinal disorders or gastrointestinal motility dysfunction, the inventors disclaim, as such, compounds of the formula

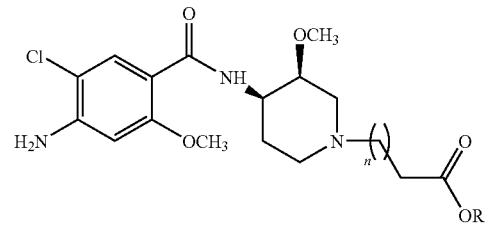

wherein R is selected from H, methyl, ethyl, isopropyl, sec-butyl, and 4-fluorophenyl and n is 0, 1, 2, 3, or 4. More typically, the inventors herein disclaim In the treatment of treating gastrointestinal disorders or gastrointestinal motility dysfunction, wherein n is from 0 to 8 and R is hydrogen, lower alkyl, or substituted aryl.

A further aspect of the invention relates to a method of treating lower urinary tract disorders, such as e.g. hyperactive bladder, comprising administering a compound of the invention.

The treatment of primary or secondary hyperaldosteronism comprising administering a compound of the invention is a further aspect of the invention. The person skilled in the art will appreciate that the compounds of the invention are applicable for use in the treatment of all diseases associated with peripheral 5-HT receptors. Thus, a further aspect of the invention relates to a method of treating a disease associated, at least in part, with a peripheral 5-HT receptor subgroup comprising administering a compound of the invention. Pharmacologically the active principle according to the invention has the advantage of facilitating absorption over the gastrointestinal membranes due to the relatively lipophilic moiety and/or nonionic moiety, such as an ester group. Subsequently to being absorbed through the biomembrane of the gastrointestinal tract the facilitating moiety is cleavaged from the active principle resulting in leaving an acid moiety on the active principle. The active principle comprising the acid moiety is then present in the blood circulation for systemic action. As a consequence of the residual acid moiety the access to the brain over the BBB is prevented.

Thus the active principle is in one aspect of the invention acting as a pro-drug facilitating the absorption over the biomembrane of the gastrointestinal tract. A further aspect of the invention relates to the systemically circulating drug that is provided with an moiety, such as an acid moiety, that prevents the absorption over the BBB.

In embodiments of the invention wherein known compounds are modified according to the invention, that is to say with an acidic moiety, the compounds of this invention are anticipated to have therapeutic properties similar to those of the unmodified parent compounds. Accordingly, dosage rates and routes of administration of the disclosed compounds are similar to those already used in the art and known to the skilled artisan (see, for example, Physicians' Desk Reference, 54th Ed., Medical Economics Company, Montvale, N.J., 2000).

Typically doses of compounds of formula III will be from about 0.1 mg to about 200 mg, in single or divided doses. Preferably, a daily dose range should be between about 1 mg to about 100 mg, in single or divided doses, while most preferably, a daily dose range should be between about 2 mg to about 75 mg, in single or divided doses. It is preferred that the doses are administered from 1 to 4 times a day. It may be necessary to use dosages outside these ranges in some cases as will be apparent to those skilled in the art.

A further aspect of the invention relates to a composition comprising a compound of the invention and a pharmaceutically acceptable excipient. The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention are formulated such that an effective amount of the bioactive compound(s) is combined with a suitable carrier in order to facilitate effective administration of the composition.

In one embodiment of the invention the active component is formulated in a pharmaceutical dosage unit. The dosage unit can be formulated for release of the active principle in the stomach. The dosage unit can be formulated for release of the active principle in the duodenum. The dosage unit can be formulated as a sustained release formulation, implying that the active principle is not immediately released. The release can be sustained to take place in the intestinal tract. In one embodiment the sustained release can take place in the small intestine. In a suitable embodiment, the sustained release takes place in the colon.

The dosage unit comprises pharmaceutically acceptable excipients. The dosage unit is typically a tablet or capsule. The dosage unit can be coated with an exipient known in the art for controlling the disintegration of the dosage unit. Such coating excipients comprises one or more of various polymers such as polymethacrylates, tributylesters, cellulose and modified celluloses, carboxymethylcellulose and salts thereof, natural and synthetic waxs, carnaubawax, polyvinylpyrrolidone, sugar alcohols, starch and modified starch, gelatine, chitosan and shellac though is not limited hereto.

In still another embodiment the release is controlled in a manner that implies for a targeted release. The dosage unit formulated as a targeted release formulation can control the release to take place at the desired site of action. The release can be controlled in a manner where a burst dose of the active principle is initially released, followed by a secondary release at a later time point and/or at another site in the gastrointestinal tract. The release can be controlled by means of pH as the pH varies in the gastrointestinal tract. Alternatively, the release can be controlled by a dosage unit that is eroded in a time dependent manner. In one embodiment the dosage unit is formulated to have a prolonged release, by which is intended that the active principle is slowly released over a longer time period compared with that of an immediate release dosage unit.

The sustained or controlled release effect can be achieved by a coating or by a matrix type of dosage unit, as is well-known in the art.

In one embodiment the tablet is a matrix type of tablet. In another embodiment the tablet is coated.

In still another embodiment the active principle is formulated to give a fast onset of action. The fast onset of action can be achieved by formulating the dosage unit in formulations that implies absorption of the active principle transmucosally. In one aspect the active principle is formulated into a buccal formulation providing the active principle to buccal absorption. A buccal formulation comprises a tablet, a sublingual tablet, a buccal patch, a buccal spray, a chewing gum.

Administration routes like nasal, transdermal and buccal administration have special advantages when treating conditions implying nausea and/or vomiting.

One embodiment of the invention relates to formulating the active principle into a formulation for nasal administration. By the nasal administration is intended a systemic action. Though administering the active principle nasally, the intention being to treat conditions peripherally and not for the active principle to cross the blood-brain-barrier. Nasal administration has the advantage of a fast onset of action. However, nasal administration is also known to provide direct access to the CNS, which is to be avoided when targetting peripheral 5-HT, particularly 5-HT4 receptors.

As can be realised by the artisan, the chemical characteristics of the active substance are such that the compound has one lipophilic site and one hydrophilic site of the molecule. The lipophilic part will tend to be readily absorbed into biological membranes. The hydrophilic part will in the circumstances that it is ionised not be readily absorbed through biological membranes. In the embodiment where the hydrophilic end comprises an acid moiety, the acid moiety will be non-ionised in an environment more acidic than the pKa value. In the embodiment where the hydrophilic site comprises a basic moiety the basic moiety will be unionised in an environment more basic than the pKa value.

In the embodiment where the hydrophilic site comprises a acid moiety the artisan will often prefer to formulate the active principle as the salt of the acid. This will also be the case in the event that the hydrophilic site comprises a basic moiety. Formulating the active principle as a salt can improve the solubility and the solubility rate. Pharmaceutical salts of basic active principles are salts of strong or medium strong acids; hydrochloric acid; sulphate; phosphate or weak acids like tartrate; acetate etc. Salts of weak acids are typically salts of sodium; potassium; or calcium.

In one embodiment the active principle is formulated in a formulation comprising lipid excipients. The lipid excipients are providing compositions wherein the active principle of the invention is encapsulated. By formulating the active principle in a lipid formulation the absorption over the biological membrane of the intestinal tract is facilitated. Once absorbed systemically the active principle will be released from the lipid formulation. The active principle will target itself to the desired site of action while being hindered to pass the BBB due to the character, such as an ionic character, of the hydrophilic moiety. In preparing the lipid formulations, lipid components including neutral lipids, positively-charged lipids, such as sphingosine and ceramide, negatively-charged lipids, amphoteric lipids such as phospholipids, and cholesterol are advantageously used. As defined herein, the "lipid component" of the compositions of the invention are intended to encompass a single species of lipid (such as a particular phospholipid) or combinations of such lipids, either of one type such as combinations of phospholipids (for example, phophatidylcholine plus phosphatidyl enthanolamine) or of different types (such as a phospholipid plus a charged lipid or a neutral lipid). Combinations comprising a multiplicity of different lipid types are also advantageously encompassed by the proliposomal compositions of the invention.

Chemical substances crosses the blood brain barrier (BBB) via differents routes such as opening of tight junctions, increased pinocytosis, decreased membrane rigidity, by pore formation or other mechanisms. There are four basic mechanisms by which solute molecules move across membranes. First is by simple diffusion, which proceeds from low to high concentrations. Secondly is by facilitated diffusion, a form of carrier-mediated endocytosis, in which solute molecules bind to specific membrane protein carriers, also from low to high concentration. Thirdly is simple diffusion through an aqueous channel, formed within the membrane. Fourthly is by active transport through a protein carrier with a specific binding site that undergoes a change in affinity. Active transport requires ATP hydrolysis and conducts movement against the concentration gradient. Movement between cells is referred to as paracellular diffusion. The BBB has a number of highly selective mechanisms for transport of nutrients into the brain.

Diffusion of substances into the brain can be divided into paracellular (i.e. between cells) and transcellular[13](i.e. across cells) diffusion, both of which are non-saturable and non-competitive. Paracellular diffusion does not occur to any great extent at the BBB, due to the "tight junctions". In the case of transcellular diffusion, the general rule is the higher the lipophilicity of a substance, the greater the diffusion into the brain. Another general rule is the smaller size of the molecule the greater the diffusion into the brain. In the present invention the active principle is chemically modified comprising a polar site that prevents the active principle from being transported into the brain. Further the transportation through the BBB can be prevented by modifying the active principle with a bulky moiety as the BBB is most permeable towards small, lipid-soluble molecules.

The compositions of the subject invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets) with the oral solid preparations being preferred over the oral liquid preparations. A preferred oral solid preparation is capsules. The most preferred oral solid preparation is tablets. Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or encapsulating materials.

The pharmaceutical compositions may be subdivided into unit doses containing appropriate quantities of the active component. The unit dosage form can be a packaged preparation, such as packeted tablets, capsules, and powders in paper or plastic containers or in vials or ampules. Also, the unit dosage can be a liquid based preparation or formulated to be incorporated into solid food products, chewing gum, or lozenge.

Any suitable route of administration may be employed for providing the patient with an effective dosage. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

When formulating the active principle into a transdermal formulation special care should be taken to select a suitable enhancer.

One aspect of the invention relates to formulating the active principle into a dosage unit that displays a stability that implies a shelf-life of the dosage units of 5 years; such as 4 years; such as 3 years; such as 2 years. In one embodiment the stability during the shelf-life is obtained by means of the packaging material. In one embodiment packaging material displays a high resistance towards water vapour.

One embodiment of the invention provides a method of treating gastroesophageal reflux disease in a mammal, while substantially reducing the concomitant adverse effects associated with the administration of the compound devoid of the acidic moiety, comprising administering to a human in need of such treatment, a therapeutically effective amount of a compound of the invention.

Yet another embodiment of the present invention provides a method of eliciting an anti-emetic effect in a mammal, while substantially reducing the adverse effects associated with the administration of the compound devoid of the acidic moiety, comprising administering to a mammal in need of such anti-emetic therapy, a therapeutically effective amount a compound of the invention.

Without being limited to examples, the invention is further directed to any one of the compounds described in the examples, having an acidic moiety and/or esters thereof. Table 1 in the Examples demonstrate the proof of concept that a representative sample of all of the compounds of the invention have a good binding affinity for the serotonin receptor.

EXAMPLES

Synthetic Chemistry

Example 1

Preparation of intermediate 2,2,2-trichloroethyl 4-bromobutyrate

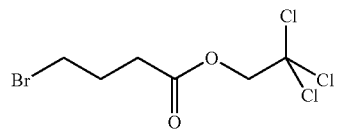

A stirred solution of 4-bromobutyric acid (3.34 g, 20.0 mmol) in toluene (50 ml) was added 2,2,2-trichloroethanol (14.94 g, 0.10 mol) and p-toluenesulfonic acid monohydrate (7.60 g, 40.0 mmol) and refluxed with a Dean-Stark trap attached for 6 h. Water was removed continuously. The reaction mixture was cooled to room temperature and concentrated in vacuo. The mixture was added $CH_2Cl_2$ (75 ml) and washed with $H_2O$ (3×25 ml). The organic layer was dried over $Na_2SO_4$, filtered and evaporated in vacuo to leave an oil. The residue was distilled to leave the title compound as a colourless oil (4.77 g, 79.9%) (bp 100° C. at 0.5 mmHg).

$^1$H-NMR (300 MHz, $CDCl_3$): δ 4.74 (s, 2H), 3.48 (t, 2 H), 2.65 (t, 2 H), 2.21-2.13 (m, 2 H)

Example 2

Preparation of intermediate 4-(4-hydroxymethyl-piperidin-1-yl)butyric acid 2,2,2-trichloroethylester

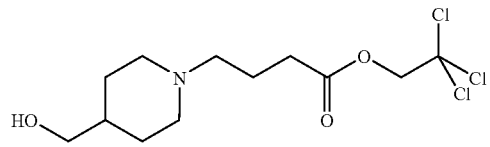

A stirred solution of 4-piperidinemethanol (1.72 g, 15.0 mmol) in acetone (100 ml) was added $K_2CO_3$ (4.14 g, 30. mmol) and 2,2,2-trichloroethyl 4-bromobutyrate (4.47 g, 15.0 mmol) and heated under reflux for 3 h. The reaction mixture was cooled to room temperature, filtered and the filtrate concentrated in vacuo. The residue was added CH$_2$Cl$_2$ (75 ml) and washed with brine (25 ml) and H$_2$O (2×25 ml). The organic layer was dried over Na$_2$SO$_4$, filtered and evaporated in vacuo to leave the title compound as a viscous oil (4.70 g, 94.1%).

$^1$H-NMR (300 MHz, CDCl$_3$): δ 4.74 (s, 2H), 3.50 (d, 2 H), 2.92 (d, 2 H), 2.52-2.35 (m, 4 H), 1.97-1.70 (m, 7 H), 1.52-1.45 (m, 1 H), 1.32-1.23 (m, 2 H)

Example 3

Synthesis of 1H-indole-3-carboxylic acid 1-[3-(2,2,2-trichloroethyl-ethoxycarbonyl)-propyl]-piperidine-4-ylmethyl ester

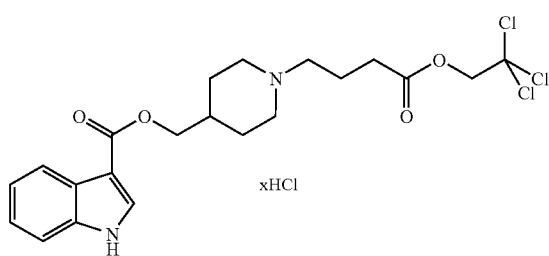

A suspension of indole-3-carboxylic acid (2.90 g, 18.0 mmol) in CH$_2$Cl$_2$ (75 ml) was treated with oxalyl chloride (1.84 ml, 20.7 mmol) and DMF (1 drop) and the mixture stirred at room temperature for 2 h, then concentrated in vacuo to leave the acid chloride as a yellow solid. This was dissolved in a mixture of CH$_2$Cl$_2$ (30 ml) and THF (10 ml) and added dropwise (30 min) to a stirred solution of 4-(4-hydroxymethyl-piperidin-1-yl)butyric acid 2,2,2-trichloroethyl ester (from example 2) (4.98 g, 15.0 mmol) and NEt$_3$ (1.82 g, 18.0 mmol) in CH$_2$Cl$_2$ (30 ml). The reaction mixture was stirred at room temperature overnight, treated with an aqueous satd. NaCl solution (25 ml) and 10% aqueous NaHCO$_3$ solution (25 ml). The organic layer was dried over Na$_2$SO$_4$, filtered and evaporated in vacuo to a brown viscous oil. The residue was separated with flash chromatography (SiO$_2$, EtOAc). The product was obtained as a pale yellow solid (1.83 g, 25.6%). Conversion to the hydrochloride salt was effected using etheral HCl.

$^1$H-NMR (300 MHz, CDCl$_3$): δ 9.02 (br s, 1 H), 8.22-8.18 (m, 1 H), 7.92 (d, 1 H), 7.48-7.41 (m, 1 H), 7.35-7.28 (m, 2 H), 4.77 (s, 2 H), 4.24 (d, 2 H) 3.03 (d, 2 H), 2.59-2.44 (q, 5 H), 2.13-1.85 (m, 7 H), 1.60-1.43 (m, 2 H)

$^{13}$C-NMR (75 MHz, CDCl$_3$): δ 171.7, 165.5, 136.2, 131.5, 125.7, 122.8, 121.7, 121.0, 111.7, 108.0, 94.8, 73.7, 67.9, 57.5, 53.1, 35.4, 31.7, 28.8, 21.8

MS (ES): 477.1 [M+H]$^+$

Example 4

Synthesis of 1H-indole-3-carboxylic acid 1-(3-carboxy-propyl)-piperidin-4-ylmethyl ester

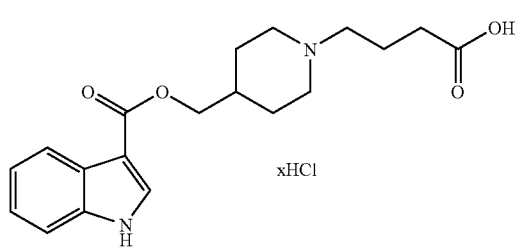

1H-indole-3-carboxylic acid 1-[3-(2,2,2-trichloroethyl-ethoxycarbonyl)-propyl]piperidine-4-ylmethyl ester (0.48 g, 1.0 mmol) was dissolved in a mixture of THF (25 ml) and aqueous 1 M KH$_2$PO$_4$ (5 ml). Zn-powder (0.66 g, 10.0 mmol) was added and the resulting mixture stirred at room temperature for 24 h. The reaction mixture was filtered through a pad of kiselguhr and the filtrate evaporated in vacuo. The residue was separated with flash chromatography (SiO$_2$, EtOAc/MeOH (2:1)). The expected product was obtained as a white solid (0.29 g, 84.2%). Conversion to the hydrochloride salt was effected using etheral HCl.

$^1$H-NMR (300 MHz, DMSO): δ 11.98 (s, 1 H), 8.08-7.97 (m, 2 H), 7.47 (d, 1 H), 7.20-7.17 (m 2 H), 4.11 (d, 2 H), 2.96 (d, 2 H), 2.50-2.37 (m, 4 H), 2.05 (t, 2 H), 1.77-1.66 (m, 6 H), 1.42-1.35 (m, 2 H)

$^{13}$C-NMR (75 MHz, DMSO): δ 171.7, 165.5, 136.2, 131.5, 125.7, 122.8, 121.7, 121.0, 111.7, 108.0, 94.8, 73.7, 67.9, 57.5, 53.1, 35.4, 31.7, 28.8, 21.8

MS (ES): 345.2 [M+H]$^+$

Example 5

Preparation of intermediate N-(1-benzylpiperidin-4-yl)napth-1-yl carboxamide

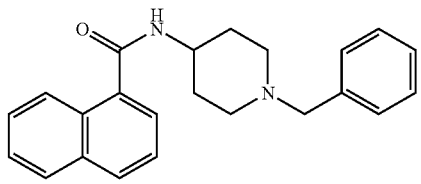

A stirred suspension of 1-napthoic acid (8.61 g, 0.050 mol) in CH$_2$Cl$_2$ (150 ml) was added SOCl$_2$ (23.79 g, 0.20 mol) and the mixture heated under reflux for 4 h. The mixture was evaporated in vacuo to leave the acid chloride as a solid material. This was dissolved in CH$_2$Cl$_2$ (150 ml) and added dropwise to a stirred solution of 4-amino-1-benzylpiperidine (9.51 g, 0.050 mol) and NEt$_3$ (5.06 g, 0.05 mol) in CH$_2$Cl$_2$ (100 ml) at 0° C. The mixture was stirred to room temperature for 24 h and washed with H$_2$0 (3×75 ml) The organic layer was dried over Na$_2$SO$_4$ and evaporated in vacuo to a solid material. This was recrystallized from ethanol/water (40/60) to leave the product as a white solid (7.8 g, 45.3%).

$^1$H-NMR (300 MHz, CDCl$_3$): δ 8.32-8.27 (m, 1 H), 7.90 (t, 2 H), 7.57-7.30 (m, 9 H), 6.17 (d, 2 H), 4.17-4.06 (m, 1 H), 3.55 (s, 2H), 2.88 (d, 2 H), 2.27-2.05 (m, 4 H), 1.69-1.50 (m, 2 H)

Example 6

Preparation of intermediate N-(piperidin-4-yl)napth-1-yl carboxamide hydrochloride

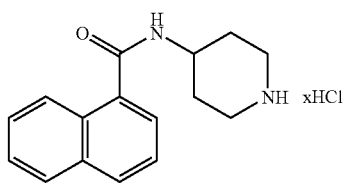

A solution of N-(1-benzylpiperidin-4-yl)napth-1-yl carboxamide (1.38 g, 4.0 mmol) in dry CH$_2$Cl$_2$ (15 ml) was cooled to 0° C. and added α-chloroethyl chloroformate (1.14 g, 8.0 mmol) and stirred for 30 minutes. The mixture was evaporated in vacuo, added MeOH (15 ml) and heated under reflux for 1 h. The reaction mixture was evaporated in vacuo and the residue recrystallized from acetonitrile to give the product as a white powder (1.01 g, 86.8%).

$^1$H-NMR (300 MHz, CDCl$_3$): δ 8.32-8.27 (m, 1 H), 7.90 (t, 2 H), 7.57-7.30 (m, 9 H), 6.17 (d, 2 H), 4.17-4.06 (m, 1 H), 3.55 (s, 2H), 2.88 (d, 2 H), 2.27-2.05 (m, 4 H), 1.69-1.50 (m, 2 H)

Example 7

Alkylation of N-(piperidin-4-yl)napth-1-yl carboxamide hydrochloride with 2,2,2-trichloroethyl 4-bromobutyrate

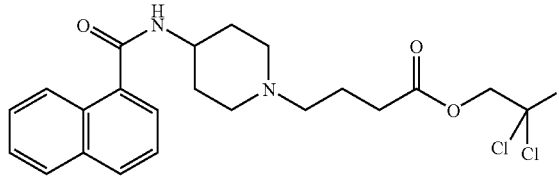

A stirred suspension of N-(piperidin-4-yl)napth-1-yl carboxamide hydrochloride (0.58 g, 2.0 mmol) in acetone (20 ml) was added K$_2$CO$_3$ (1.10 g, 8.0 mmol) and 2,2,2-trichloroethyl 4-bromobutyrate-(0.89 g, 3.0 mmol) and heated under reflux for 24 h. The mixture was cooled to room temperature and filtered. The filtrate was evaporated in vacuo and the residue added CH$_2$Cl$_2$ (50 ml) and washed with H$_2$0 (3×25 ml). The organic layer was dried over Na$_2$SO$_4$, filtered and evaporated in vacuo to an oil. The oil was separated with flash chromatography (SiO$_2$, EtOAc/MeOH (1:1)) to give the product as a white solid (0.87 g, 92.2%).

$^1$H-NMR (200 MHz, CDCl$_3$): δ 8.26-8.21 (m, 1 H), 7.83 (t, 2 H), 7.56-7.37 (m, 4 H), 5.89 (d, 2 H), 4.71 (s, 2 H), 4.17-4.06 (m, 1 H), 2.84 (d, 2 H), 2.49 (t, 2 H), 2.39 (t, 2 H), 2.21-2.11 (m, 4 H), 1.93-1.82 (p, 2 H), 1.62-1.49 (m, 2 H)

$^{13}$C-NMR (75 MHz, CDCl$_3$): δ 173.0, 168.4, 134.1, 133.0, 129.8, 129.4, 127.7, 126.4, 125.6, 124.8, 124.2, 124.1, 73.8, 60.0, 57.0, 52.0, 46.5, 31.6, 22.0, 14.1

MS (ES): 494.2 [M+Na]$^+$

Example 8

Hydrolysis of the Trichloroethyl Ester from Example 7

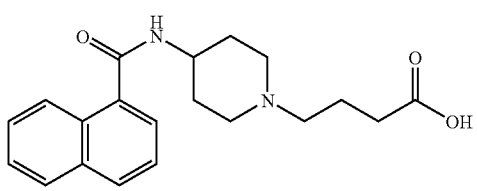

Following the procedure outlined in example 4, the trichloroethyl ester from example 7 (0.67 g, 1.4 mmol) was converted to the title compound as a white solid (0.38 g, 79.6%).

$^1$H-NMR (200 MHz, DMSO-$_{d6}$): δ 8.50 (d, 2 H), 8.39-8.18 (m, 1 H), 8.04-7.96 (m, 2 H), 7.62-7.50 (m, 4 H), 3.91 (br s, 1 H), 2.93 (d, 2 H), 2.37 (t, 2 H), 2.23-2.06 (m, 4 H), 1.92 (d, 2 H), 1.72-1.57 (m, 4 H)

$^{13}$C-NMR (50 MHz, DMSO-$_{d6}$): δ 167.9, 135.1, 133.0, 129.7, 129.5, 128.1, 126.6, 126.1, 125.3, 125.0, 124.9, 57.4, 52.0, 46.6, 38.6, 33.5, 31.2, 22.2

MS (ES): 363.1 [M+Na]$^+$

Example 9

Alkylation of N-(piperidin-4-yl)napth-1-yl carboxamide hydrochloride with ethyl 4-bromobutyrate

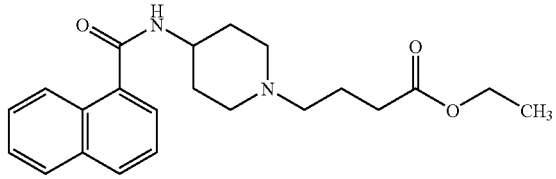

Following the procedure outlined in example 7, N-(piperidin-4-yl)napth-1-yl carboxamide hydrochloride 6 (0.58 g, 2.0 mmol) was converted to the title compound as a white solid (0.67 g, 91.4%).

$^1$H-NMR (300 MHz, CDCl$_3$): δ 8.24 (d, 1 H), 7.89-7.82 (m, 2 H), 7.54-7.49 (m, 3 H), 7.40 (t, 1 H), 6.07 (d, 2 H), 4.14-4.07 (m, 3 H), 2.84 (d, 2 H), 2.36-2.28 (m, 4 H), 2.13-2.04 (m, 4 H), 1.81-1.76 (p, 2 H), 1.55-1.51 (m, 2 H), 1.26 (t, 3 H)

$^{13}$C-NMR (75 MHz, CDCl$_3$): δ 173.3, 168.7, 134.5, 133.4, 130.2, 129.8, 128.1, 126.8, 126.1, 125.1, 124.6, 124.5, 60.1, 57.4, 52.1, 46.9, 32.0, 22.2, 14.0

MS (ES): 391.2 [M+Na]$^+$

Example 10

Preparation of intermediate (piperidin-4-yl)ethylcarboxylate hydrochloride

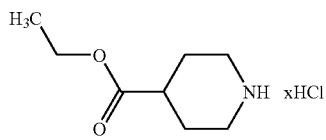

To a stirred solution of isonipectoic acid (12.9 g, 0.10 mol) in absolute ethanol (200 ml) was cooled to 0° C. and SOCl$_2$ (47.5 g, 0.40 mol) dropwise added. The mixture was stirred to room temperature and heated to reflux for 3 h. The reaction mixture was evaporated in vacuo and the residue dissolved in a 10% aqueous solution of NaOH (250 ml). The aqueous solution was extracted with CH$_2$Cl$_2$ (3×100 ml). The organic extracts was dried over NaSO$_4$, filtered and evaporated in vacuo. The residue was dissolved in dry ethanol and HCl bubbled into the solution to give the hydrochloride precipitate. The residue was recrystallized from absolute ethanol to give the product as a white solid (17.46 g, 90.2%).

¹H-NMR (300 MHz, CDCl₃): δ 9.40 (br s, 2 H), 4.09-4.02 (q, 2 H), 3.30 (d, 2 H), 3.01-2.95 (m, 2 H), 2.56-2.47 (m, 1 H), 2.14-1.95 (m, 4 H), 1.30 (t, 3 H)

Example 11

Preparation of intermediate (1-benzylpiperidin-4-yl)ethylcarboxylate hydrochloride

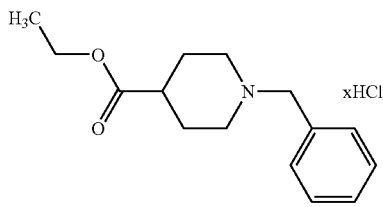

A suspension of (piperidin-4-yl)ethylcarboxylate hydrochloride (8.6 g, 44.4 mmol) and K₂CO₃ (24.5 g, 0.17 mol) in acetone (200 ml) was added benzylbromide (9.11 g, 53.3 mmol) and heated to reflux for 12 h. The solvent was evaporated in vacuo and the residue added H₂O (200 ml). The aqueous layer was extracted with Et₂O (3×100 ml) and the organic extracts dried over Na₂SO₄, filtered and evaporated in vacuo. The residue was dissolved in acetone and HCl bubbled into the solution to give the hydrochloride precipitate. The precipitate was filtered, dried and recrystallized from acetone to give the expected product as a white solid (11.03 g, 87.6%).

¹H-NMR (300 MHz, DMSO-$d_6$): δ 11.48 (br s, 1 H), 7.67 (s, 2 H), 7.42 (s, 3 H), 4.30-4.25 (m, 2 H), 4.11-4.01 (m, 2 H), 3.28 (d, 2 H), 2.97-2.84 (m, 2 H), 2.15-1.99 (m, 4 H) 1.15 (t, 3 H)

Example 12

Preparation of intermediate 1-[(1-benzylpiperidin-4-yl)methanol

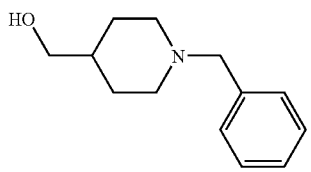

A suspension of LiAlH₄ (1.52 g, 40.0 mmol) in dry THF (30 ml) was stirred at 0° C. and dropwise added a solution of 1-benzylpiperidin-4-yl)ethylcarboxylate hydrochloride (2.47 g, 10.0 mmol) in dry THF (50 ml). The obtained mixture was heated under reflux for 4 h and then cooled to room temperature. EtOAc (200 ml), water (40 ml), and a 2 N aqueous solution of NaOH (10 ml) were added. The obtained mineral precipitate was filtered through a pad of kiselguhr, the filtrate evaporated in vacuo and water (50 ml) added to the residue. The aqueous layer was extracted with CH₂Cl₂ (3×50 ml) and the organic extracts combined and dried over Na₂SO₄, filtered and evaporated in vacuo to give the product as a colourless oil (1.75 g, 85.6%)

¹H-NMR (200 MHz, CDCl₃): δ 7.40-7.26 (m, 5 H), 3.53-3.46 (m, 4 H), 2.94 (d, 2 H), 2.61 (br s, 1 H), 2.00 (t, 2 H), 1.75 (d, 2 H), 1.48-1.26 (m, 3 H)

Example 13

Synthesis of 1-[(1-benzylpiperidin-4-yl)carboxymethyl]napthalene

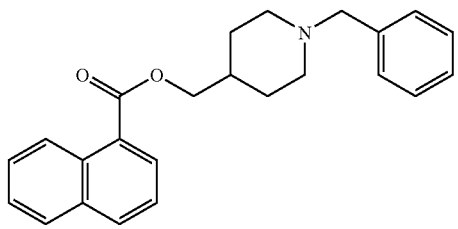

A stirred solution of (1-benzylpiperidin-4-yl)methanol (2.79 g, 13.7 mmol) and NEt₃ (1.65 g, 16.3 mmol) in CH₂Cl₂ (50 ml) was cooled to 0° C. and dropwise added a solution of napthoyl chloride (prepared as in example 7) (3.11 g, 16.3 mmol) dissolved in CH₂Cl₂/THF (1:1, 50 ml). The resulting mixture was stirred to room temperature overnight, evaporated in vacuo and the residue added EtOAc (100 ml). The organic layer washed with water (50 ml), brine (50 ml) and water (50 ml). The organic layer was dried over Na₂SO₄, filtered and evaporated in vacuo to give an oil. The oil was separated with flash chromatography (SiO₂, EtOAc) to give the expected product as a yellow oil (3.12 g, 63.3

¹H-NMR (300 MHz, CDCl₃): δ 8.94 (d, 1 H), 8.22-8.19 (m, 1 H), 8.04 (d, 1 H), 7.90 (d, 1 H), 7.64-7.49 (m, 3 H), 7.49-7.25 (m, 5 H), 4.30 (d, 2 H), 3.52 (s, 2 H), 2.98 (d, 2 H), 2.09-2.00 (m, 2 H), 1.93-1.83 (m, 3 H), 1.57-1.45 (m, 2 H)

MS (ES): 360.1 [M+H]⁺

Example 14

Preparation of intermediate 1-[(piperidin-4-yl)methyloxycarbonyl]napthalene hydrochloride

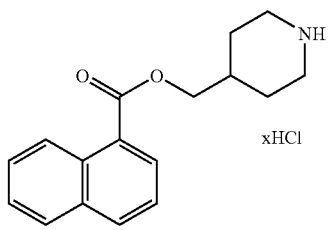

Following the procedure outlined in Example 6, 1-[(1-benzylpiperidin-4-yl)carboxymethyl]napthalene (1.69 g, 4.70 mmol) was converted to the title compound as a yellow solid (1.07 g, 74.5%).

¹H-NMR (300 MHz, CDCl₃): δ 9.60 (br s, 2 H), 8.86 (d, 1 H), 8.17 (d, 1 H), 8.00 (d, 1 H), 7.85 (d, 1 H), 7.61-7.34 (m, 3 H), 4.28 (d, 2 H), 3.55 (d, 2 H), 2.89 (d, 2 H), 2.04-1.68 (m, 5 H)

Example 15

Alkylation of 1-[(piperidin-4-yl)methyloxycarbonyl]napthalene hydrochloride with 2,2,2-trichloroethyl 4-bromobutyrate

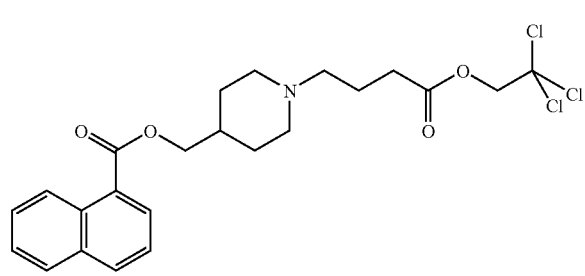

Following the procedure outlined in Example 7, 1-[(piperidin-4-yl)methyloxycarbonyl]napthalene hydrochloride (0.30 g, 1.0 mmol) was converted to the title compound as a white solid (0.43 g, 89.5%).

¹H-NMR (300 MHz, CDCl₃): δ 8.89 (d, 1 H), 8.18-8.14 (m, 1 H), 8.00 (d, 1 H), 7.88-7.84 (m, 1 H), 7.63-7.43 (m, 3 H), 4.72 (s, 2 H), 4.24 (d, 2 H), 2.93 (d, 2 H), 2.49 (t, 2 H), 2.38 (t, 2 H), 1.96-1.79 (m, 8 H), 1.46-1.27 (m, 2 H)

¹³C-NMR (75 MHz, CDCl₃): δ 171.9, 167.5, 133.8, 133.2, 131.3, 130.0, 128.5, 127.7, 127.2, 126.1, 125.7, 124.4, 95.0, 73.9, 69.3, 60.3, 57.7, 53.3, 35.5, 31.9, 29.1, 22.1, 21.0, 14.1

MS (ES): 487.1 [M+H]⁺

Example 16

Alkylation of 1-[(piperidin-4-yl)methyloxycarbonyl]napthalene hydrochloride with ethyl 4-bromobutyrate

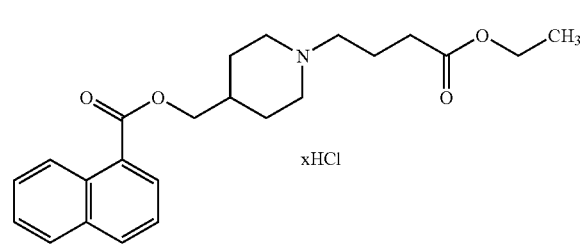

Following the procedure outlined in example 7, 1-[(piperidin-4-yl)methyloxycarbonyl]napthalene hydrochloride (0.39 g, 1.27 mmol) was converted to the title compound as a yellow oil. The oil was dissolved in Et₂O and HCl bubbled into the solution to give the hydrochloride precipitate. The precipitate was filtered off, dried and recrystallized from acetonitrile to leave the hydrochloride salt (0.31 g, 73.8%).

¹H-NMR (300 MHz, DMSO-$d_6$): δ 10.7 (br s, 1 H), 8.76 (d, 1 H), 8.23 (t, 2 H), 8.04 (d, 1 H), 7.71-7.59 (m, 3 H), 4.28 (d, 2 H), 4.11-4.03 (q, 2 H), 3.49 (d, 2 H), 3.51-2.96 (m, 5 H), 2.41 (t, 2 H), 2.00-1.83 (m, 7 H), 1.19 (t, 3 H)

¹³C-NMR (75 MHz, DMSO-$d_6$): δ 172.8, 167.4, 134.4, 134.2, 131.3, 131.0, 129.6, 128.8, 127.3, 127.2, 125.8, 125.7, 68.6, 60.9, 56.0, 52.0, 33.7, 31.4, 26.4, 19.6, 14.9

MS (ES): 406.2 [M+Na]⁺

Example 17

Hydrolysis of the Trichloroethyl Ester from Example 16

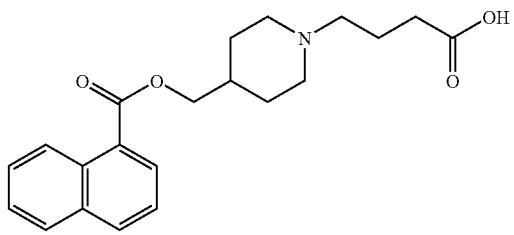

Following the procedure outlined in example 4, the trichloroethyl ester from example 16 (0.43 g, 0.88 mmol) was converted to the title compound as a white solid (0.25 g, 79.9

¹H-NMR (300 MHz, DMSO-$d_6$): δ 10.11, 8.75 (d, 1 H), 8.15 (t, 2 H), 8.01 (d, 1 H), 7.68-7.57 (m, 3 H), 4.20 (d, 2 H), 2.90 (d, 2 H), 2.33 (t, 2 H), 2.20 (t, 2 H), 2.03-1.92 (t, 2 H), 1.75-1.60 (m, 5 H), 1.45-1.30 (m, 2 H)

¹³C-NMR (75 MHz, DMSO-$d_6$): δ 175.0, 166.6, 133.4, 133.3, 130.4, 129.8, 128.6, 127.8, 126.7, 126.3, 125.0, 124.8, 68.7, 57.4, 52.3, 34.7, 33.2, 28.0, 21.6

MS (ES): 378.1 [M+Na]⁺

Example 18

Alkylation of 1-[(piperidin-4-yl)methyloxycarbonyl]napthalene hydrochloride with diethyl 2-bromoethylphosphonate

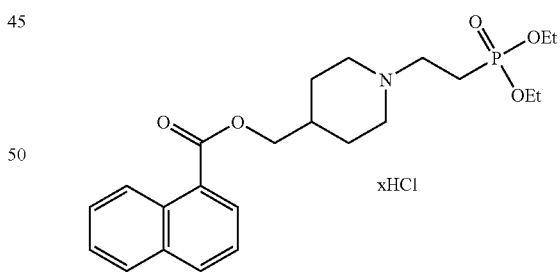

Following the procedure outlined in example 7, 1-[(piperidin-4 yl)methyloxycarbonyl]-napthalene hydrochloride (0.63 g, 2.06 mmol) was converted to the title compound as a yellow oil. The oil was dissolved in Et₂O and HCl bubbled into the solution to give a white precipitate. The precipitate was filtered off, dried and recrystallized from acetonitrile to leave the hydrochloride salt (0.37 g, 37.9%)

¹H-NMR (300 MHz, DMSO-$d_6$): δ 11.0 (br s, 1 H), 8.78 (d, 1 H), 8.28-8.21 (m, 2 H), 8.09-8.05 (m, 1H), 4.30 (d, 2 H), 4.14-4.03 (q, 4 H), 3.63-3.52 (m, 2 H), 3.20-2.95 (m, 5 H), 2.48-2.37 (m, 1 H), 2.02-1.81 (m, 5 H), 1.28 (t, 6 H)

$^{13}$C-NMR (75 MHz, DMSO-$_{d6}$): δ 166.5, 133.4, 133.3, 130.4, 130.1, 128.7, 127.9, 126.4, 126.3, 124.9, 124.8, 67.7, 61.6, 61.5, 50.7, 50.0, 32.9, 26.5, 21.1, 19.3, 16.2, 16.1

MS (ES): 456.2 [M+N]$^+$

Example 19

Preparation of intermediate N-(1-benzylpiperidin-4-yl)-indazole-3-carboxamide

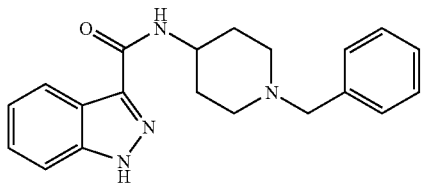

A stirred solution of 1-H-indazole-3-carboxylic acid (8.11 g, 50.0 mmol) in dry DMF (140 ml) under argon atmosphere was added CDI (8.92 g, 55 mmol) and heated at 60° C. for 2 h. The mixture was cooled to room temperature, dropwise added 4-amino-1-benzylpiperidine (9.51 g, 50.0 mmol) previously dissolved in DMF (20 ml). The mixture was heated at 60° C. for 2 h, cooled to room temperature and the solvent evaporated in vacuo. The residue was added CH$_2$Cl$_2$ (250 ml) and the organic layer washed with H$_2$O (100 ml), 1 N aqueous NaOH (100 ml), H$_2$O (100 ml) and brine (100 ml). The organic layer was dried over Na$_2$SO$_4$, filtered and evaporated in vacuo. The residue was recrystalilized from EtOH to leave the expected product as a white solid (14.23 g, 85.1%).

$^1$H-NMR (200 MHz, DMSO-$_{d6}$): δ 13.59, 8.20 (t, 2 H), 7.61 (t, 1 H), 7.38-7.21 (m, 7 H), 3.95-3.87 (m, 1 H), 3.49 (s, 2 H), 2.80 (d, 2 H), 2.04 (t, 2 H), 1.78-1.67 (4 H)

Example 20

Preparation of intermediate N-(1-benzylpiperidin-4-yl)-1-isopropylindazole-3-carboxamide

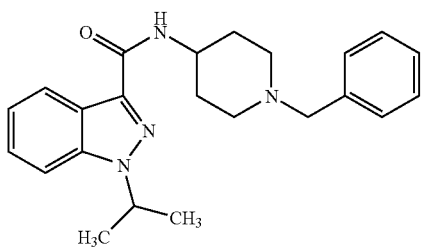

A solution of N-(1-benzylpiperidin-4-yl)-indazole-3-carboxamide (3.34 g, 10.0 mmol) in dry DMF (70 ml) under argon atmosphere was added sodium hydride (0.25 g, 10.0 mmol) and stirred at room temperature for 3 h. The mixture was added isopropylbromide (1.37 g, 11.0 mmol) and stirred for additional 24 h. The reaction mixture was evaporated in vacuo and the residue added EtOAc (100 ml). The organic layer washed with brine (50 ml) and H$_2$O (2×50 ml). The organic layer was dried over Na$_2$SO$_4$, filtered and evaporated in vacuo to leave an oil that solidified upon standing. The oil was separated with flash chromatography (SiO$_2$, Et$_2$O/Hexane (2:1) to leave the product as a solid (1.22 g, 32.7%).

$^1$H-NMR (200 MHz, CDCl$_3$): δ 8.40 (d, 1 H), 7.44-7.27 (m, 8 H), 6.95 (d, 1 H), 4.92-4.83 (p, 1 H), 4.05-3.95 (m, 1 H), 3.55 (s, 1 H), 2.91 (d, 2 H), 2.21 (t, 2 H), 2.08 (d, 2 H), 1.71-1.60 (m, 8 H)

Example 21

Preparation of intermediate N-(1-piperidin-4-yl)-1-isopropylindazole-3-carboxamide hydrochloride

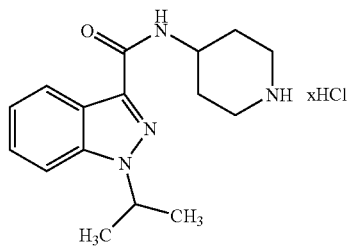

Following the procedure outlined in Example 6, N-(1-benzylpiperidin-4-yl)-1-isopropylindazole-3-carboxamide (1.77 g, 4.28 mmol) was converted to the title compound as a white solid (1.26 g, 91.1%).

$^1$H-NMR (200 MHz, CDCl$_3$): δ 9.80 (br s, 1 H), 9.68 (br s, 1 H), 8.34 (d, 1 H), 7.49-7.31 (m, 2 H), 7.28-7.26 (m, 1 H), 7.05 (d, 1 H), 4.94-4.85 (m, 1 H), 4.35-4.32 (m, 1 H), 3.62 (d, 2 H), 3.15-3.04 (m, 2 H), 2.36-2.32 (m, 2 H), 2.18-2.08 (m, 3 H), 1.65 (d, 6 H)

Example 22

Alkylation of N-(1-piperidin-4-yl)-1-isopropylindazole-3-carboxamide hydrochloride with ethyl 4-bromobutyrate

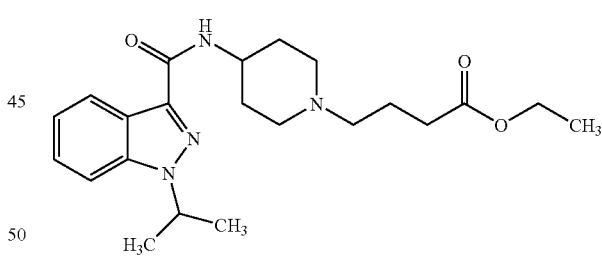

Following the procedure outlined in Example 7, N-(1-piperidin-4-yl)-1-isopropylindazole-3-carboxamide hydrochloride (0.32 g, 1.0 mmol) was converted to the title compound as a colourless oil (0.37 g, 93.7%).

$^1$H-NMR (300 MHz, CDCl$_3$): δ 8.38 (d, 1 H), 7.43-7.37 (m, 3 H), 7.26 (d, 1 H), 4.90-4.82 (m, 1 H), 4.19-4.08 (m, 1 H), 2.91 (d, 2 H), 2.43-2.31 (m, 4 H), 2.19-2.03 (m, 5 H), 1.87-1.58 (m, 11 H), 1.26 (t, 3 H)

$^{13}$C-NMR (75 MHz, CDCl$_3$): δ173.3, 162.0, 139.8, 136.7, 126.2, 122.8, 122.7, 122.2, 109.1, 60.1, 57.4, 52.3, 50.7, 46.0, 32.2, 32.1, 22.2, 21.9, 14.1

MS (ES): 423.1 [M+Na$^+$]

Conversion to the hydrochloride salt was effected using ethereal HCl.

Example 23

Alkylation of N-(1-piperidin-4-yl)-1-isopropylindazole-3-carboxamide hydrochloride with 2,2,2-trichloroethyl 4-bromobutyrate

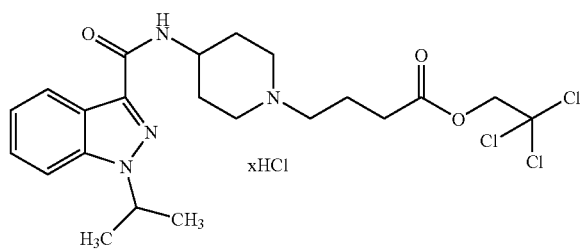

A stirred suspension of N-(1-piperidin-4-yl)-1-isopropylindazole-3-carboxamide hydrochloride (0.32 g, 1.0 mmol) and K$_2$CO$_3$ (0.55 g, 4.0 mmol) in acetone (15 ml) was added 2,2,2-trichloroethyl 4-bromobutyrate (0.45 g, 1.5 mmol) and heated under reflux for 12 h. The mixture was cooled to room temperature, filtered and the filtrate evaporated in vacuo. The residue was added EtOAc (30 ml) and the organic layer washed with H$_2$O (15 ml), brine (15 ml) and H$_2$O (15 ml). The organic layer was dried over Na$_2$SO$_4$, filtered and the solvent evaporated in vacuo to leave an oil. The oil was dissolved in acetone and dropwise added 1.0 M HCl in Et$_2$O to give a white precipitate. The precipitate was filtered off, dried and recrystallized from acetone to leave the hydrochloride salt as a white powder (0.47 g, 87.0%).

$^1$H-NMR (300 MHz, CDCl$_3$): δ 12.44 (br s, 1 H), 8.29 (d, 1 H), 7.47-7.37 (m, 2 H), 7.25 (t, 1 H), 7.16 (d, 1 H), 4.89-4.85 (m, 1 H), 4.76 (s, 2 H), 4.19-4.08 (m, 1 H), 3.71 (d, 2H), 3.14-2.69 (m, 4 H), 2.34-2.03 (m, 8 H), 1.61 (d, 6 H)

$^{13}$C-NMR (75 MHz, CDCl$_3$): δ170.3, 162.4, 139.9, 135.9, 126.4, 122.8, 122.6, 122.3, 109.3, 94.6, 74.0, 56.2, 52.2, 50.9, 43.8, 30.7, 29.1, 22.0, 18.9, 15.2

MS (ES): 526.2 [M+Na]$^+$

Example 24

Hydrolysis of the Trichloroethyl Ester from Example 23

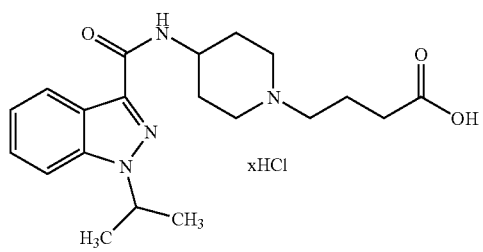

Following the example outlined in example 4, the trichloroethyl ester from example 23 (0.37 g, 0.69 mmol) was converted to the title compound as a white solid (0.20 g, 77.9

$^1$H-NMR (300 MHz, CD$_3$OD): δ 8.21 (d, 1 H), 7.61 (d, 1 H), 7.42-7.37 (m, 1 H), 7.24 (t, 1 H), 5.01-4.93 (m, 1 H), 4.24-4.19 (m, 1 H), 3.51 (d, 2 H), 3.05-2.91 (m, 4 H), 2.45 (t, 2 H), 2.18-2.14 (m, 2 H), 1.99-1.88 (m, 4 H), 1.57 (d, 6 H)

$^{13}$C-NMR (75 MHz, CD$_3$OD): δ 181.1, 164.5, 141.4, 137.6, 127.6, 124.0, 123.7, 123.0, 110.9, 59.1, 52.6, 52.1, 45.6, 37.4, 30.5, 22.3, 21.7

MS (ES): 395.1 [M+Na]$^+$

Example 25

Preparation of intermediate 4-bromomethyl benzoic acid 2,2,2-trichloroethyl ester

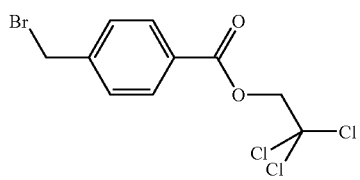

A solution of 2,2,2-trichloroethanol (2.46 g, 16.5 mmol) and NEt$_3$ (1.67 g, 16.5 mmol) in CH$_2$Cl$_2$ (40 ml) at 0° C. was dropwise added 4-bromomethyl benzoylbromide (4.17 g, 15.0 mmol) in CH$_2$Cl$_2$ (20 ml) and stirred to room temperature overnight. The reaction mixture was added H$_2$O (20 ml) and the organic layer separated. The organic layer washed with aqueous 1 M HCl (20 ml) and H$_2$O (20 ml). The organic layer was dried over Na$_2$SO$_4$, filtered and the solvent evaporated in vacuo to leave the expected product as a white solid. The product was used directly in the next step without any further purification (to be filled in).

$^1$H-NMR (300 MHz, CDCl$_3$): δ 7.86 (dd, 4 H), 5.00 (s, 2 H), 4.54 (s, 2 H)

Example 26

Alkylation of N-(1-piperidin-4-yl)-1-isopropylindazole-3-carboxamide hydrochloride with 4-bromomethyl benzoic acid 2,2,2-trichloroethyl ester

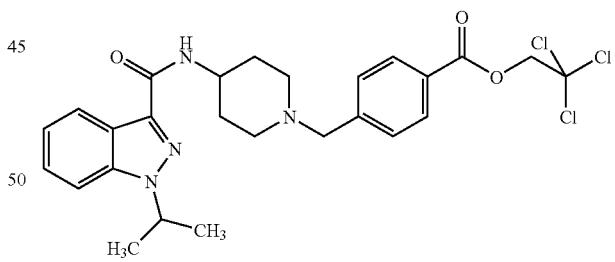

Following the procedure outlined in Example 7, N-(1-piperidin-4-yl)-1-isopropylindazole-3-carboxamide hydrochloride (0.41 g, 1.3 mmol) was converted to the title compound as a colourless oil (0.61 g, 85.2%).

$^1$H-NMR (300 MHz, CDCl$_3$): δ 8.38 (d, 1 H), 8.09 (d, 2 H), 7.50-7.36 (m, 4 H), 7.29-7.23 (m, 1 H), 6.95 (d, 1 H) 4.98 (s, 2 H), 4.92-4.83 (p, 1 H), 4.13-4.04 (m, 1 H), 3.60 (s, 2 H), 2.88 (d, 2 H), 2.24 (t, 2 H), 2.10-2.05 (m, 2 H), 1.75-1.61 (m, 8 H), $^{13}$C-NMR (75 MHz, CDCl$_3$): δ 165.2, 162.6, 145.9, 140.3, 137.3, 130.5, 129.3, 128.1, 127.8, 126.7, 123.4, 123.3, 122.8, 109.8, 95.6, 74.7, 63.0, 53.0, 51.3, 46.4, 32.8, 22.5

MS (ES): 551.1 [M+H]$^+$

Example 27

Hydrolysis of the Trichloroethyl Ester from Example 26

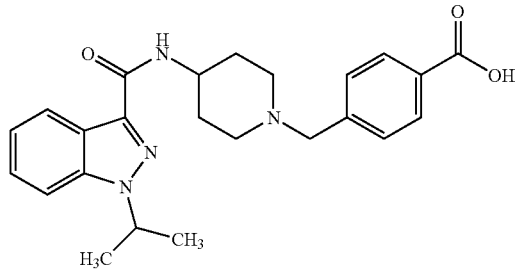

Following the procedure outlined in Example 4, the trichloroethyl ester from example 26 (0.42 g, 0.76 mmol) was converted to the title compound as a white solid (0.25 g, 78.9

$^1$H-NMR (300 MHz, CD$_3$OD): δ 8.22 (d, 1 H), 8.04 (d, 1 H), 7.66 (d, 1 H), 7.48-7.41 (m, 3 H), 7.26 (t, 1 H), 5.08-4.99 (m, 1 H), 4.10-4.03 (m, 1H), 3.13 (d, 2 H), 2.53 (t, 2 H), 2.08-2.04 (m, 2 H), 1.92-1.85 (m, 2 H), 1.61 (d, 2 H)

$^1$H-NMR (75 MHz, CD$_3$OD): δ 163.5, 140.4, 136.7, 129.7, 126.6, 123.0, 122.6, 122.0, 109.9, 61.7, 52.2, 51.1, 46.0, 30.6, 21.3

MS (ES): 419.1 [M+H]$^+$

Example 28

Preparation of intermediate 4-aminomethyl-1-(tert-butoxycarbonyl)piperidine

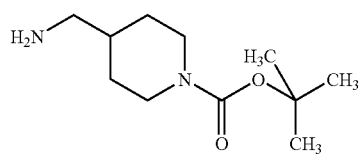

Benzaldehyde (8.73 g, 82.3 mmol) was added all at once to a stirred solution of 4-aminomethylpiperidine (9.42 g, 82.3 mmol) in toluene (100 ml). The mixture was heated under reflux for 4 h with a Dean-Stark trap attached to collect the water. The reaction mixture was cooled to room temperature and di-tert-butyldicarbonate (19.75 g, 90.5 mmol) was added in divided portions under continuously stirring. The mixture was stirred overnight, evaporated in vacuo and the residue stirred vigorously with aqueous 1 N KHSO$_4$ (100 ml) at room temperature for 4 h. The mixture was extracted with Et$_2$O (3×100 ml) and then the aqueous layer was made strongly basic with NaOH. The aqueous layer was extracted with CH$_2$Cl$_2$ (3×100 ml). The combined extracts were dried with Na$_2$SO$_4$, filtered and the solvent evaporated in vacuo to leave the product as an oil (15.4 g, 86.5%).

$^1$H-NMR (200 MHz, DMSO-$_{d6}$): δ 4.04-4.01 (m, 2 H), 2.60 (t, 2 H), 2.50 (d, 2 H), 1.62 (d, 2 H), 1.32 (s, 9 H), 1.31-1.28 (m, 1 H), 1.06 (br s, 2 H), 1.03-0.93 (m, 2 H)

Example 29

Synthesis of 4-amino-N-(tert-butoxycarbonyl)piperidin-4-ylmethyl]-5-chloro-2-methoxybenzamide

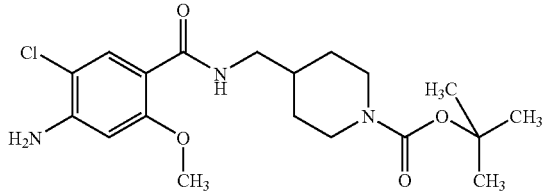

A mixture of 4-aminomethyl-1-(tert-butoxycarbonyl)piperidine (10.0 g, 46.7 mmol), 4-amino-5-chloro-2-methoxybenzoic acid (9.41 g, 46.7 mmol) and NEt$_3$ (6.80 ml, 46.7 mmol) in DMF (100 ml) were added 1-ethyl-3-[3-(dimethylamino)propyl]carbodiimide hydrochloride (EDC) (9.39 g, 46.7 mmol) and 1-hydroxybenzotriazole (HOBT) (6.62 g, 46.7 mmol) at 0° C. The reaction mixture was stirred to room temperature overnight and concentrated in vacuo. The resulting residue was added H$_2$O (100 ml) and extracted with EtOAc. The combined organic extracts were washed with aqueous K$_2$CO$_3$ and dried over Na$_2$SO$_4$. The solvent was removed in vacuo and the residue separated with flash chromatography (SiO$_2$, EtOAc) to give the expected product as a white solid (11.91 g, 64.1%).

$^1$H-NMR (200 MHz, CDCl$_3$): δ 8.06 (s, 1 H), 7.77 (t, 1 H), 6.33 (s, 1 H), 4.64 (s, 2 H), 4.08 (d, 2 H), 3.86 (s, 3 H), 3.30 (t, 2 H), 2.67 (t, 2 H), 1.78-1.66 (m, 3 H), 1.43 (s, 9 H), 1.24-1.11 (m, 2 H)

Example 30

Preparation of intermediate 4-amino-5-chloro-2-methoxy-N-(piperidin-4-ylmethyl)benzamide hydrochloride

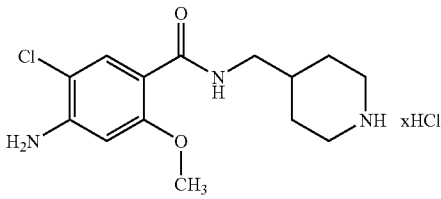

A stirred solution of 4-amino-N-(tert-butoxycarbonyl)piperidin-4-ylmethyl]-5-chloro-2-methoxybenzamide (1.70 g, 4.3 mmol) in 1,4-dioxane (30 ml) at 0° C. was added 4 M HCl in 1,4-dioxane (10 ml) in portions. The reaction mixture was stirred to room temperature for 4 h, evaporated in vacuo and the residue recrystallized from acetone to leave the product as a red solid (0.89 g, 61.8%).

$^1$H-NMR (300 MHz, DMSO-$_{d6}$): δ 9.28 (br s, 1 H), 9.04 (br s, 1 H), 8.00 (t, 1 H), 7.64 (s, 1 H), 7.31 (br s, 4 H), 6.58 (s, 1 H), 3.81 (s, 3 H), 3.21-3.16 (m, 4 H), 2.82-2.71 (q, 2 H), 1.80-1.71 (m, 3 H), 1.45-0.34 (m, 2 H)

Example 31

Alkylation of 4-amino-5-chloro-2-methoxy-N-(piperidin-4-ylmethyl)benzamide hydrochloride with ethyl 4-bromobutyrate

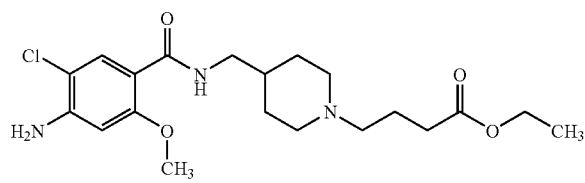

Following the method outlined in Example 7, 4-Amino-5-chloro-2-methoxy-N-(piperidin-4-ylmethyl)benzamide hydrochloride (0.76 g, 1.98 mmol) was converted to the title compound as an oil (0.57 g, 69.9%).

$^1$H-NMR (300 MHz, CDCl$_3$): δ 8.08 (s, 1 H), 7.74 (t, 1 H), 6.30 (s, 1 H), 4.49 (s, 2 H), 4.14-4.07 (q, 2 H), 3.87 (s, 3 H), 3.30 (t, 2 H), 2.90 (d, 2 H), 2.35-2.28 (m, 4 H), 1.94-1.69 (m, 7 H), 1.29-1.18 (m, 5 H)

$^{13}$C-NMR (75 MHz, CDCl$_3$): δ 173.9, 164.9, 157.7, 147.0, 133.4, 112.9, 111.9, 98.2, 66.2, 58.3, 56.5, 53.8, 45.5, 36.5, 32.7, 30.4, 15.6

MS (ES): 411.9 [M+H]$^+$

Conversion to the hydrochloride salt was effected with ethereal HCl.

Example 32

Alkylation of 4-amino-5-chloro-2-methoxy-N-(piperidin-4-ylmethyl)benzamide hydrochloride with diethyl 2-bromoethylphosphonate

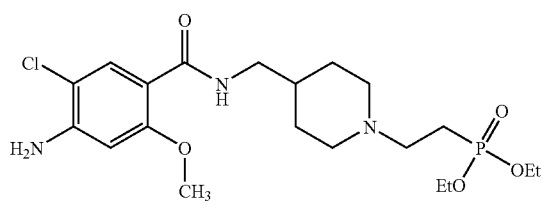

Following the procedure outlined in Example 7, 4-Amino-5-chloro-2-methoxy-N-(piperidin-4-ylmethyl)benzamide hydrochloride (1.53 g, 4.0 mmol) was converted to the title compound as an oil (1.12 g, 57.1%).

$^1$H-NMR (300 MHz, CDCl$_3$): δ 7.99 (s, 1 H), 7.70 (t, 1 H), 6.29 (s, 1 H), 4.66 (s, 2 H), 4.08-3.97 (m, 4 H), 3.80 (s, 3 H), 3.24 (t, 2 H), 2.83 (d, 2 H), 2.58-2.53 (m, 2 H), 1.96-1.84 (m, 4 H), 1.66 (d, 2 H), 1.55-1.47 (m, 1 H), 1.30-1.22 (m, 8 H)

$^{13}$C-NMR (75 MHz, CDCl$_3$): δ 165.0, 157.7, 147.6, 133.1, 112.3, 111.6, 98.1, 61.9, 56.4, 53.2, 52.0, 45.3, 36.4, 29.5, 24.9, 23.1, 16.8

MS 462.1 [M+H]$^+$

Conversion to the hydrochloride salt was effected using ethereal HCl.

Example 33

Preparation of intermediate 1-benzyl-4-carbonylamide piperidine

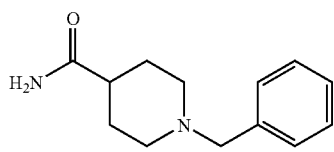

A stirred suspension of isonipectamide (16.5 g, 0.13 mol) and K$_2$CO$_3$ (35.6 g, 0.26 mol) in EtOH (350 ml) was added benzylbromide (22.0 g, 0.13 mol) and heated under reflux for 3 h, cooled to room temperature and filtered. The filtrate was evaporated in vacuo and added H$_2$O (200 ml). The aqueous layer was extracted with CH$_2$Cl$_2$ (3×150 ml), the organic layers combined and dried over Na$_2$SO$_4$ and filtered. The solvent was evaporated in vacuo to leave the product as a white solid (20.0 g, 71.0%).

$^1$H-NMR (300 MHz, CDCl$_3$): δ 7.34-7.21 (m, 5 H), 6.36 (br s, 1 H), 5.80 (br s, 1 H), 3.49 (s, 2 H), 2.92 (d, 2 H), 2.14-1.99 (m, 1 H), 1.96 (t, 2 H), 1.85-1.72 (m, 4 H)

Example 34

Preparation of intermediate 1-benzyl-4-cyano-piperidine

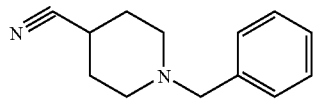

1-Benzyl-4-carbonylamide piperidine (20.0 g, 91.7 mmol) was mixed with P$_2$O$_5$ (16.92, 119.2 mmol) and heated under argon at 180-200° C. for 3 h, cooled to room temperature and added H$_2$O (150 ml). The aqueous solution was basified by careful addition of K$_2$CO$_3$ and then extracted with EtOAc (3×150 ml). The organic extracts were dried over Na$_2$SO$_4$, filtered and the solvent evaporated in vacuo to leave a yellow oil (16.7 g, 90.9%).

$^1$H-NMR (200 MHz, CDCl$_3$): δ 7.41-7.25 (m, 5 H), 3.53 (s, 2 H), 2.75-2.64 (m, 2 H), 2.40-2.34 (m, 2 H), 1.98-1.86 (m, 5 H)

Example 35

Preparation of intermediate 1-benzyl-4-aminomethylpiperidine

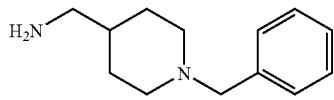

A suspension of LiAlH$_4$ (4.84 g, 0.128 mol) in dry Et$_2$O (40 ml) under argon atmosphere at 0° C. was dropwise added a solution of 1-benzyl-4-cyano-piperidine (18.3 g, 91.5 mmol) in dry Et$_2$O (80 ml) and stirred to room temperature for 24 h. The reaction mixture was treated carefully with H$_2$O (10 ml), 10% aqueous NaOH (10 ml) and H$_2$O (30 ml) to give a mineral precipitate. The precipitate was filtered through a pad of kieselguhr, washed with Et$_2$O and the filtrate evaporated in vacuo to leave the product as an oil (21.4 g, 82.3%).

$^1$H-NMR (200 MHz, CDCl$_3$): δ 7.37-7.22 (m, 5 H), 6.42 (br s, 1 H), 5.84 (br s, 1 H), 3.51 (s, 2 H), 2.94 (d, 2 H), 2.16-1.67 (m, 7 H)

Example 36

Preparation of intermediate methyl 2-(3-chloropropoxy)indole-3-carboxylate

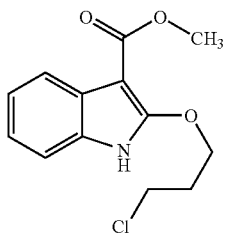

A suspension of methyl indole-3-carboxylate (5.25 g, 30.0 mmol) and DABCO (1.84 g, 16.4 mmol) in dry CH$_2$Cl$_2$ (25 ml) was cooled to 0° C. under argon atmosphere, treated in one portion with NCS (4.41 g, 33.0 mmol) and the mixture stirred for 10 min. The resulting solution was added to a solution of 3-chloropropan-1-ol (3.12 g, 33.0 mmol) in dry CH$_2$Cl$_2$ (25 ml) containing anhydrous methane sulphonic acid (0.23 ml). The resulting suspension was stirred for 30 min and then washed with 10% aqueous Na$_2$CO$_3$ solution (3×25 ml). The organic layer was dried over Na$_2$SO$_4$, filtered and concentrated in vacuo. The resulting oil was triturated with toluene (10 ml) at 0° C. for 1 h and the solid precipitate filtered, washed with a small amount of toluene and dried in vacuo to leave the product as an off-white solid (5.22 g, 65.0%).

$^1$H-NMR (200 MHz, CDCl$_3$): δ 9.51 (s, 1 H), 8.04 (d, 1 H), 7.28-7.14 (m, 3 H), 4.49 (t, 2 H), 3.96 (s, 3 H), 3.67 (t, 2 H), 2.18-2.10 (m, 2 H)

Example 37

Preparation of intermediate methyl 3,4-dihydro-2H-[1,3]oxazino[3,2-a]indole-10-carboxylate

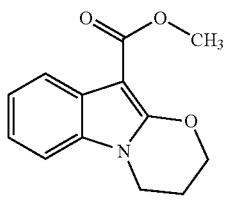

Methyl 2-(3-chloropropoxy)indole-3-carboxylate (5.0 g, 18.7 mmol) was added to a stirred mixture of 5.4 M aqueous M NaOH (3.8 ml) and toluene (50 ml) and heated at 40° C. for 4 h. The aqueous layer was separated and the organic layer washed with H$_2$O (3×25 ml) while maintaining the temperature at 60° C. The organic solvent was evaporated in vacuo to leave the product as a white solid (4.0 g, 93.2%).

$^1$H-NMR (200 MHz, CDCl$_3$): δ 8.0 (dd, 1 H), 7.24-7.12 (m, 3 H), 4.50 (t, 2 H), 4.06 (t, 2 H), 3.91 (s, 3 H), 2.34-2.26 (m, 2 H)

Example 38

Preparation of intermediate 3,4-dihydro-N-[1-(phenylmethoxy)-4-piperidinyl]methyl]-2H-[1,3]oxazino[3,2-a]indole-10-carboxamide

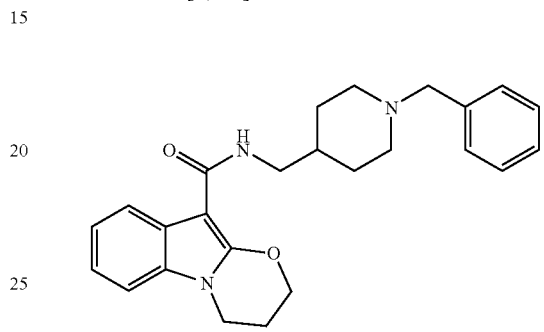

Trimethylaluminium (2 M in toluene, 9 ml) was diluted with dry toluene (9 ml) and the solution cooled to 0° C. under argon atmosphere. 1-Benzyl-4-aminomethylpiperidine (from example 37) (3.37 g, 16.5 mmol) was added to the solution, followed by methyl 3,4-dihydro-2H-[1,3]oxazino[3,2-a]indole-10-carboxylate (from example 39) (3.81 g, 16.5 mmol). The reaction mixture was heated under reflux for 5 h, cooled to room temperature and 10% aqueous NaOH solution (40 ml) dropwise added. The toluene layer washed with H$_2$O, brine and evaporated in vacuo to give an oil. The residue was purified by flash chromatography (SiO$_2$, CH$_2$Cl$_2$/MeOH (7:3)) to leave the product as an off white solid (3.52 g, 53.4%).

$^1$H-NMR (300 MHz, DMSO-d$_6$): δ 8.34 (d, 1 H), 7.33-7.06 (m, 8 H), 6.53 (t, 1 H), 4.49 (t, 2 H), 4.04 (t, 2 H), 3.51 (s, 3 H), 3.34 (t, 2 H), 2.92 (d, 2 H), 2.36-2.28 (q, 2 H), 2.03-1.95 (m, 2 H), 1.78-1.62 (m, 3 H), 1.43-1.34 (m, 2 H)

Example 39

Preparation of intermediate 3,4-dihydro-N-[4-piperidinyl]methyl]-2H-[1,3]oxazino[3,2-a]indole-10-carboxamide

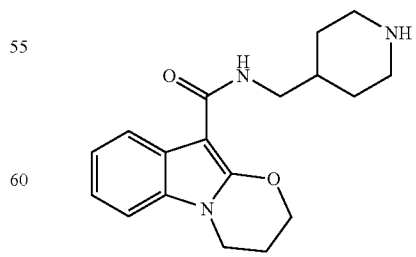

A stirred solution of 3,4-dihydro-N-[1-(benzyl)-4-piperidinyl]methyl]-2H-[1,3]oxazino[3,2-a]indole-10-carboxamide (2.01 g, 5.0 mol) in EtOH (20 ml) was added hydrazine monohydrate (0.36 ml) and 10% palladium on activated charcoal (M-type, 0.40 g) and heated under reflux for 2 h. The reaction mixture was cooled to room temperature, filtered through a pad of kiselguhr and the filtrate evaporated in vacuo to leave the expected product as a white solid (1.52 g, 97.3%).

$^1$H-NMR (200 MHz, DMSO-$d_6$): δ 8.09-8.05 (m, 1 H), 7.31-7.27 (m, 1 H), 7.14-7.03 (m, 2 H), 6.81 (t, 1 H), 4.59 (t, 1 H), 4.23-4.17 (m, 1 H), 4.11 (t, 2 H), 3.17 (t, 2 H), 3.0 (d, 2 H), 2.56-2.45 (m, 2 H), 2.35-2.24 (m, 2 H), 1.66-1.61 (m, 3 H), 1.23-1.04 (m, 2 H)

Example 40

Alkylation of 3,4-dihydro-N-[4-piperidinyl]methyl]-2H-[1,3]oxazino[3,2-a]indole-10-carboxamide with ethyl 4-bromobutyrate

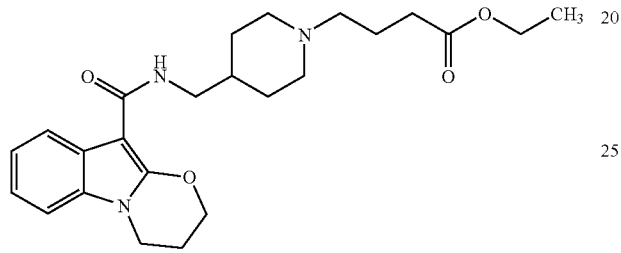

Following the procedure outlined in Example 7, 3,4-dihydro-N-[4-piperidinyl]methyl]-2H-[1,3]oxazino[3,2-a]indole-10-carboxamide (0.62 g, 2.0 mmol) was converted to the title compound as a colourless oil that crystallized upon standing (0.74 g, 86.5%).

$^1$H-NMR (300 MHz, CDCl$_3$): δ 8.33 (d, 1 H), 7.25-7.10 (m, 3 H), 6.56 (t, 1 H), 4.55 (t, 2 H), 4.14-4.10 (m, 4 H), 3.34 (t, 2 H), 2.98 (d, 2 H), 2.43-2.31 (m, 6 H), 2.01 (t, 2 H), 1.91-1.81 (m, 4 H), 1.73-1.66 (m, 1 H), 1.42-1.37 (m, 2 H), 1.26 (t, 3 H)

$^{13}$C-NMR (75 MHz, CDCl$_3$): δ 173.4, 164.8, 149.2, 131.0, 125.6, 122.1, 121.0, 120.6, 107.4, 89.2, 66.8, 60.2, 57.8, 53.4, 44.2, 38.9, 36.1, 32.2, 29.7, 22.0, 21.2, 14.2

MS (ES): 450.1 [M+Na]$^+$

Conversion to the HCl-salt was effected with etheral HCl. The precipitate was collected and recrystallized from acetone to leave the HCl-salt as a white crystalline solid.

Example 41

Alkylation of 3,4-dihydro-N-[4-piperidinyl]methyl]-2H-[1,3]oxazino[3,2-a]indole-10-carboxamide with methyl 6-bromohexanoate

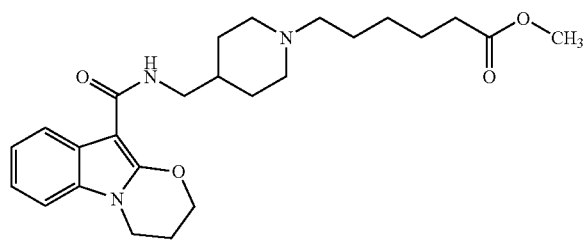

Following the procedure outlined in Example 7, 3,4-dihydro-N-[4-piperidinyl]methyl]-2H-[1,3]oxazino[3,2-a]indole-10-carboxamide (0.31 g, 1.0 mmol) was converted to the title compound as a white solid (0.37 g, 84.5%).

$^1$H-NMR (300 MHz, CDCl$_3$): δ 8.33 (d, 1 H), 7.23-7.09 (m, 3 H), 6.56 (t, 1 H), 4.54 (t, 2 H), 4.10 (t, 2 H), 3.67 (s, 3 H), 3.34 (t, 2 H), 2.97 (d, 2 H), 2.38-2.29 (m, 6 H), 1.96 (t, 2 H), 1.79 (d, 2 H), 1.70-1.30 (m, 10 H)

$^{13}$C-NMR (75 MHz, CDCl$_3$): δ 174.1, 164.7, 149.1, 131.0, 125.5, 122.0, 121.0, 120.6, 107.4, 89.1, 66.8, 58.7, 53.5, 51.4, 44.3, 38.9, 36.2, 33.9, 29.8, 27.1, 26.4, 24.7, 21.2,

MS (ES): 464.2 [M+Na]$^+$

Example 42

Alkylation of 3,4-dihydro-N-[4-piperidinyl]methyl]-2H-[1,3]oxazino[3,2-a]indole-10-carboxamide with 2,2,2-trichloroethyl 4-bromobutyrate

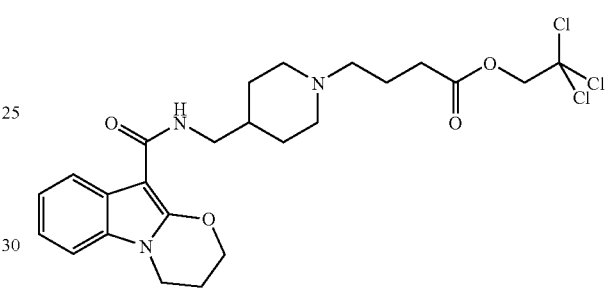

Following the procedure outlined in Example 7, 3,4-dihydro-N-[4-piperidinyl]methyl]-2H-[1,3]oxazino[3,2-a]indole-10-carboxamide (0.31 g, 1.0 mmol) was converted to the title compound as a white solid (0.40 g, 75.8%).

$^1$H-NMR (300 MHz, CDCl$_3$): δ 8.32 (d, 1 H), 7.27-7.14 (m, 3 H), 6.63 (t, 1 H), 4.77 (s, 2 H), 4.59 (t, 2 H), 4.15 (t, 2 H), 3.38 (t, 2 H), 3.22 (d, 2 H), 2.70 (t, 2 H), 2.59 (t, 2 H), 2.40-2.10 (m, 4 H), 2.05-1.96 (m, 2 H), 1.91-1.85 (m, 3 H), 1.77-1.60 (m, 2 H)

$^{13}$C-NMR (75 MHz, CDCl$_3$): δ 171.7, 166.4, 149.8, 131.5, 125.9, 122.6, 121.2, 121.1, 107.9, 95.2, 89.4, 74.3, 67.3, 57.4, 53.4, 44.2, 39.4, 35.5, 31.8, 28.8, 21.6, 21.1

MS (ES): 553.2 [M+Na]$^+$

Example 43

Hydrolysis of the Ethyl Ester from Example 40

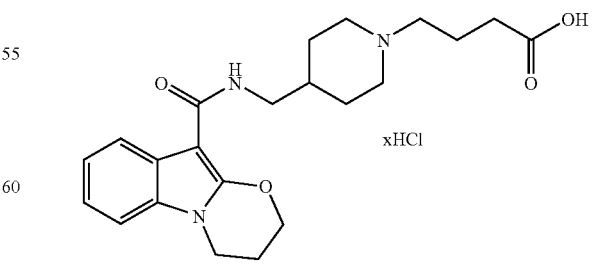

The ethyl ester from example 40 (0.51 g, 1.20 mmol) was added to a mixture of 2 M aqueous NaOH solution (1.2 ml) and MeOH (5 ml) and refluxed for 2 h. The reaction mixture was cooled to room temperature, concentrated in vacuo and dropwise added 10% aqueous HCl to pH 2. The precipitate was filtered off, washed with water and dried in vacuo to a white crystalline solid (0.31 g, 72.9%).

$^1$H-NMR (300 MHz, DMSO-$_{d6}$): δ 12.31 (br s, 1 H), 10.25 (br s, 1 H), 8.10-8.04 (m, 1 H), 7.32-7.26 (m, 1 H), 7.14-7.04 (m, 2 H), 6.96 (t, 1 H), 4.59 (t, 2 H), 4.15 (t, 2 H), 3.43-3.01 (m, 8 H), 2.38-2.28 (m, 4 H), 1.97-1.81 (m, 5 H), 1.68-1.55 (m, 2 H)

$^{13}$C-NMR (75 MHz, DMSO-$_{d6}$): δ 174.3, 164.6, 150.6, 131.8, 126.1, 122.0, 120.7, 120.4, 109.3, 88.7, 67.9, 56.1, 52.4, 43.7, 34.9, 31.5, 27.7, 21.4, 19.7

MS (ES): 398.1 [M+H]$^+$

Example 44

Alkylation of 3,4-dihydro-N-[4-piperidinyl]methyl]-2H-[1,3]oxazino[3,2-a]indole-10-carboxamide with diethyl 2-bromoethylphosphonate

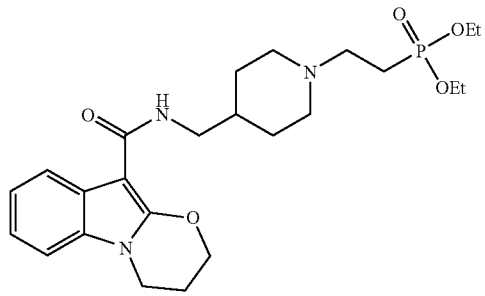

Following the procedure outlined in Example 7, 3,4-dihydro-N-[4-piperidinyl]methyl]-2H-[1,3]oxazino[3,2-a]indole-10-carboxamide (0.29 g, 0.92 mmol) was converted to the title compound as a white solid (0.36 g, 82.9%).

$^1$H-NMR (300 MHz, CDCl$_3$): δ 8.30 (d, 1 H), 7.23-7.10 (m, 3 H), 6.59 (t, 1 H), 4.56 (t, 2 H), 4.17-4.06 (m, 6 H), 3.35 (t, 2 H), 3.09 (d, 2 H), 2.86-2.78 (q, 2 H), 2.39-2.33 (m, 2 H), 2.27-2.08 (m, 4 H), 1.88-1.60 (m, 3 H), 1.58-1.50 (m, 2 H), 1.33 (t, 6 H)

$^{13}$C-NMR (75 MHz, CDCl$_3$): δ 163.5, 149.8, 131.5, 125.9, 122.5, 121.3, 121.1, 107.9, 89.4, 67.3, 62.4, 62.3, 53.2, 52.1, 44.3, 39.4, 35.9, 29.3, 21.6, 16.9, 16.8

MS (ES): 500.1 [M+Na]$^+$

Example 45

Preparation of intermediate N-[1-(benzyl)-4-piperidinyl]methyl]-1,4-benzodioxane-5-carboxamide

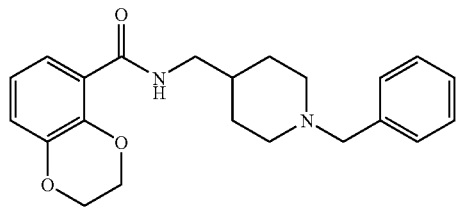

A suspension of 1,4-benzodioxan-5-carboxylic acid (1.80 g, 10.0 mmol) and 1,1'-carbonyldiimidazole (1.78 g, 11.0 mmol) in CH$_3$CN (100 ml) was stirred at room temperature for 2 h. 1-Benzyl-4-aminomethylpiperidine (from example 37) (2.04 g, 10.0 mmol) in CH$_3$CN (10 ml) was added to the mixture and stirred overnight at room temperature. The reaction mixture was concentrated in vacuo, added EtOAc (200 ml) and washed with H$_2$O (3×50 ml). The organic layer was dried over Na$_2$SO$_4$ and evaporated in vacuo to a solid material. The residue was separated with flash chromatography (SiO$_2$, EtOAc:MeOH, 1:1) to leave the product as a white solid (2.31 g, 63.1%).

$^1$H-NMR (200 MHz, CDCl$_3$): δ 7.74 (dd, 1 H), 7.67 (t, 1 H), 7.34-7.15 (m, 5 H), 7.03-6.89 (m, 2 H), 4.43-4.39 (m, 2 H), 4.33-4.29 (m, 2 H), 3.52 (s, 2 H), 3.37 (t, 2 H), 2.93 (d, 2 H), 2.06-1.93 (m, 2 H), 1.77-1.50 (m, 3 H), 1.47-1.28 (m, 2 H)

Example 46

Preparation of intermediate N-[4-piperidinyl]methyl]-1,4-benzodioxane-5-carboxamide hydrochloride

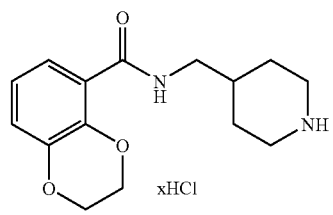

Following the procedure outlined in example 6, N-[1-(benzyl)-4-piperidinyl]methyl]-1,4-benzodioxane-5-carboxamide (1.88 g, 5.13 mmol) was converted to the title compound as an white solid (1.36 g, 85.20%).

$^1$H-NMR (300 MHz, CDCl$_3$): δ 9.68 (br s, 1 H), 9.37 (br s, 1 H), 7.79 (t, 1 H), 7.71-7.68 (dd, 1 H), 7.03-6.91 (m, 2 H), 4.47-4.45 (m, 2 H), 4.34-4.31 (m, 2 H), 3.52 (d, 2 H), 3.40 (t, 2 H), 2.94-2.82 (q, 2 H), 2.12-1.69 (m, 5 H)

Example 47

Alkylation of N-[4-piperidinyl]methyl]-1,4-benzodioxane-5-carboxamide hydrochloride with ethyl 4-bromobutyrate

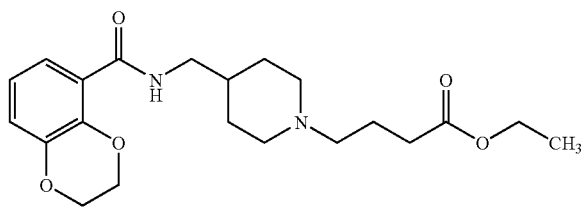

Following the procedure outlined in example 7, N-[4-piperidinyl]methyl]-1,4-benzodioxane-5-carboxamide hydrochloride (0.56 g, 2.0 mmol) was converted to the title compound as an oil (0.66 g, 85.3%).

$^1$H-NMR (300 MHz, CDCl$_3$): δ 7.74-7.71 (dd, 1 H), 7.66 (t, 1 H), 7.01-6.90 (m, 2 H), 4.44-4.41 (m, 2 H), 4.33-4.30 (m, 2 H), 4.16-4.09 (q, 2 H), 3.35 (t, 2 H), 2.92 (d, 2 H), 2.38-2.30 (m, 4 H), 2.02-1.50 (m, 7 H), 1.38-1.27 (m, 2 H), 1.25 (t, 3 H)

Example 48

Alkylation of N-[4-piperidinyl]methyl]-1,4-benzo-dioxane-5-carboxamide hydrochloride with diethyl 2-bromoethylphosphonate

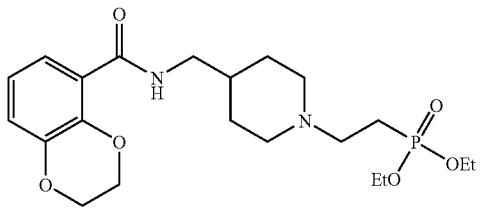

Following the procedure outlined in example 7, N-[4-piperidinyl]methyl]-1,4-benzodioxane-5-carboxamide hydrochloride (0.71 g, 2.5 mmol) was converted to the title compound as an white solid (0.88 g, 80.7%).

$^1$H-NMR (300 MHz. CDCl$_3$): δ 7.74-7.71 (dd, 1 H), 7.66 (t, 1 H), 6.98-6.93 (m, 2 H), 4.43-4.41 (m, 2 H), 4.33-4.30 (m, 2 H), 4.12-4.05 (m, 6 H), 3.35 (t, 2 H), 2.92 (d, 2 H), 2.58-2.45 (m, 2 H), 2.08-1.90 (m, 4 H), 1.71-1.50 (m, 3 H), 1.36-1.31 (m, 6 H)

$^1$H-NMR (75 MHz. CDCl$_3$): δ 165.2, 143.9, 142.3, 135.7, 127.6, 124.5, 122.6, 121.7, 121.0, 65.3, 63.9, 62.0, 61.9, 53.3, 52.1, 45.5, 36.3, 30.3, 16.7

MS (ES): 463.2 [M+Na]$^+$

Example 49

Preparation of intermediate N-[1-(benzyl)-4-piperidinyl]methyl]indole-3-carboxamide

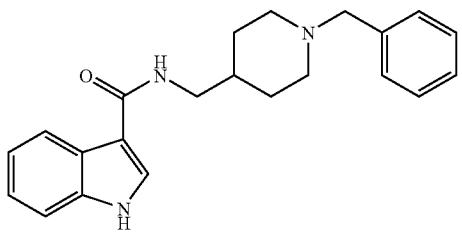

Following the procedure outlined in example 3, indole-3-carboxylic acid (5.56 g, 31.0 mmol) was converted to the title compound as an oil (3.78 g, 35.0%).

$^1$H-NMR (300 MHz, CDCl$_3$): δ 9.96 (s, 1 H), 7.96 (d, 1 H), 7.67 (s, 1 H), 7.44-7.22 (m, 8 H), 6.24 (t, 1 H), 3.51 (s, 2 H), 3.40 (t, 2 H), 2.92 (d, 2 H), 1.98 (t, 2 H), 1.78-1.67 (m, 3 H), 1.44-1.30 (m, 2 H)

$^{13}$C-NMR (75 MHz, CDCl$_3$): δ 173.5, 164.8, 143.4, 141.8, 124.0, 122.2, 121.3, 120.5, 64.9, 63.5, 60.2, 57.9, 53.3, 45.2, 36.0, 32.3, 29.9, 22.2, 14.1

MS (ES): 413.2 [M+Na]$^+$

Example 50

Preparation of intermediate N-[4-piperidinyl]methyl]indole-3-carboxamide

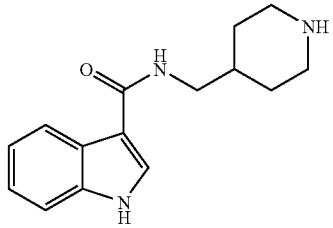

Following the procedure outlined in example 39, N-[(1-benzyl-4-piperidinyl)methyl]indole-3-carboxamide (1.50 g, 4.3 mol) was converted to the title compound as a white solid (1.07 g, 96.7%).

$^1$H-NMR (300 MHz, DMSO-$d_6$): δ 11.56 (br s, 1 H), 8.15-8.12 (m, 1 H), 8.03 (s, 1 H), 7.85 (t, 1 H), 7.41 (d, 1 H), 7.15-7.08 (m, 2 H), 3.12 (t, 2 H), 2.92 (d, 2 H), 2.55-2.49 (m, 1 H), 2.41 (t, 2 H), 1.64-1.60 (m, 3 H), 1.06-1.01 (m, 2 H)

Example 51

Alkylation of N-[4-piperidinyl]methyl]indole-3-carboxamide with ethyl 4-bromobutyrate

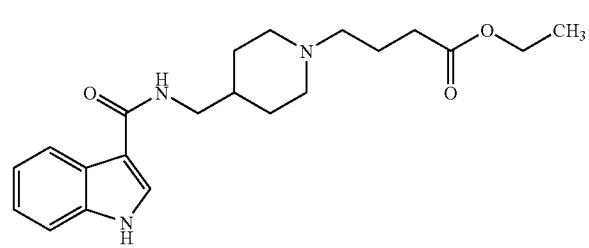

Following the procedure outlined in example 9, N-[4-piperidinyl]methyl]indole-3-carboxamide (0.24 g, 0.94 mol) was converted to the title compound as a white solid (0.16 g, 47.1%).

$^1$H-NMR (300 MHz, CDCl$_3$): δ 9.70 (br s, 1 H), 8.00-7.95 (m, 1 H), 7.78 (s, 1 H), 7.49-7.44 (m, 1 H), 7.30-7.25 (m, 2 H), 6.33 (t, 1 H), 4.20-4.09 (q, 2 H), 3.40 (t, 2 H), 2.97 (d, 2 H), 2.44-2.31 (m, 4 H), 1.99-1.76 (m, 7 H), 1.43-1.24 (m, 5 H)

$^{13}$C-NMR (75 MHz, CDCl$_3$): δ 173.4, 165.7, 136.4, 128.1, 124.7, 122.7, 121.4, 119.8, 112.1, 60.3, 57.8, 53.2, 44.8, 36.1, 32.2, 29.7, 21.9, 14.2

MS (ES): 394.1 [M+Na]$^+$

Example 52

Alkylation of N-[4-piperidinyl]methyl]indole-3-carboxamide with 2,2,2-trichloroethyl 4-bromobutyrate

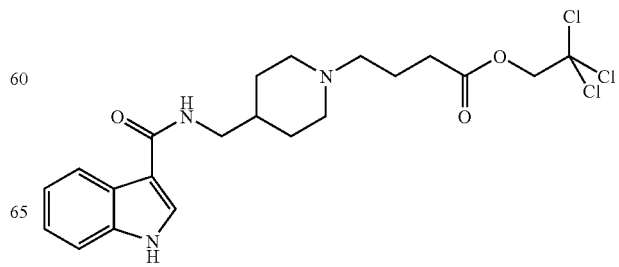

Following the procedure outlined in example 7, N-[4-piperidinyl]methyl]indole-3-carboxamide (0.94 g, 3.65 mmol) was converted to the title compound as a white solid (0.84 g, 48.4%).

$^1$H-NMR (300 MHz, CDCl$_3$): δ 10.08 (br s, 1 H), 7.95-7.92 (m, 1 H), 7.72 (s, 1 H), 7.43 7.40 (m, 1 H), 7.23-7.20 (m, 2 H), 6.31 (t, 1 H), 4.15 (s, 2 H), 3-36 (t, 2 H), 2.90 (d, 2 H), 2.36-2.17 (m, 4 H), 1.89 (t, 2 H), 1.83-1.65 (m, 5 H), 1.36-1.32 (m, 2 H)

$^{13}$C-NMR (75 MHz, CDCl$_3$): δ 173.9, 166.0, 136.5, 128.4, 124.6, 122.6, 121.4, 119.6, 112.2, 111.7, 99.7, 57.8, 53.2, 51.5, 44.9, 36.1, 32.0, 30.8, 29.7, 21.9

MS (ES): 497.2 [M+Na]$^+$

Example 53

Hydrolysis of the Trichloroethyl Ester from Example 52

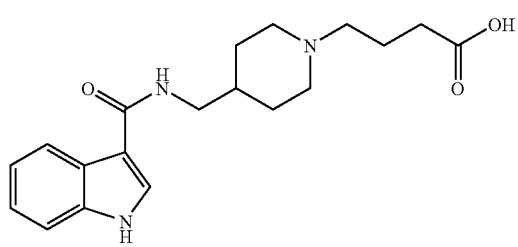

Following the procedure outlined in example 4, the trichloroethyl ester from example 52 (0.47 g, 1.0 mmol) was converted to the title compound as a white solid (0.21 g, 61.1%).

$^1$H-NMR (300 MHz, DMSO-$d_6$): 11.63 (s, 1 H), 8.13 (d, 1 H), 8.05 (d, 1 H), 7.97 (t, 1 H), 7.41 (d, 1 H), 7.15-7.05 (m, 2 H), 3.14 (t, 2 H), 3.02 (d, 2 H), 2.50 (t, 2 H), 2.26 (t, 2 H), 2.17 (t, 2 H), 1.75-1.53 (m, 5 H), 1.31-1.21 (m, 2 H)

$^{13}$C-NMR (75 MHz, DMSO-d$_6$): δ 174.4, 164.6, 136.0, 127.5, 126.1, 121.6, 120.9, 120.1, 111.7, 110.5, 57.0, 52.2, 43.6, 35.5, 33.4, 28.7, 20.9

MS (ES): 366.2 [M+Na]$^+$

Example 54

Tegaserod

Preparation of the primary amine 2,2,2-trichloroethyl 5-aminopentanoate

A stirred solution of 2,2,2-trichloroethyl 5-bromopentanoate (prepared by the same method as in example 1) in acetone is added potassium phtalimide and stirred overnight. The reaction mixture is filtered and the solvent evaporated in vacuo. The residue is added EtOAc and washed with H$_2$O. The organic layer is dried over Na$_2$SO$_4$, filtered and evaporated in vacuo to leave the title compound. Standard hydrazinolysis in EtOH gives the primary amine (see scheme 1).

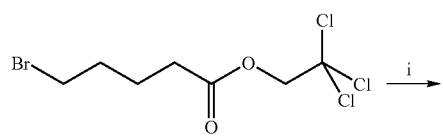

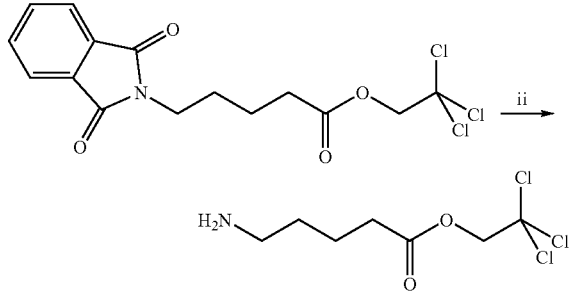

Scheme 1. i, Potassium pthalimide, acetone, ii, NH$_2$NH$_2$, EtOH

Example 55

Tegaserod

Preparation of the monoalkylated amine N-2,2,2-(trichloroethyl pentanoate)-N'-aminoguanidine A suspension of thiosemicarbamide is added MeI in EtOH and heated at 60° C. for ½ h and cooled to room temperature. The resulting suspension is filtered and the filtrate washed with Et$_2$O to leave S-methyl isothiosemicarbazide hydroiodide. S-methyl isothiosemicarbazide hydroiodide is used in the next step without any further purification. A solution of this compound in MeOH is added 2,2,2-trichloroethyl 5-aminopentanoate (from example 54) and heated under reflux overnight. The reaction mixture is cooled to room temperature and the solvent evaporated in vacuo to leave the title compound. The amine is used in the next step without any further purification (scheme 2).

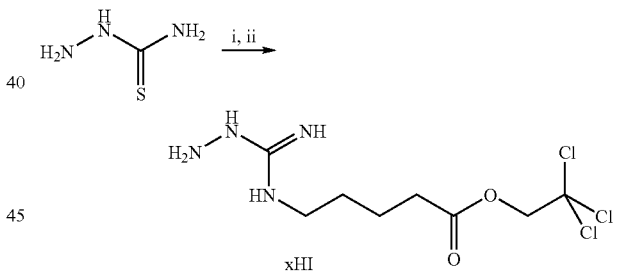

Scheme 2. i, MeI, EtOH, ii, 2,2,2-trichloroethyl 5-aminopentanoate, MeOH

Example 56

Tegaserod

Synthesis of the Tegaserod Derivative

To a stirred solution of 5-methoxyindole-3-carboxaldehyde in MeOH is added N-2,2,2-(trichloroethyl pentanoate)-N'-aminoguanidine at room temperature. The solution is acidified with conc. aqueous HCl and stirred overnight. The solvent is evaporated in vacuo and added MeOH. The solution is added etheral HCl and the precipitate filtered off. The precipitate is recrystallized from MeOH/Et$_2$O to leave the HCl salt of the trichloroethyl ester. This compound is added to a suspension of Zn and a mixture of 1 M aqueous KH$_2$PO$_4$ and THF and stirred overnight. The suspension is filtered through a pad of kiselguhr and the solvent evaporated in vacuo. The residue is separated with flash chromatography to leave the title compound as a free acid.

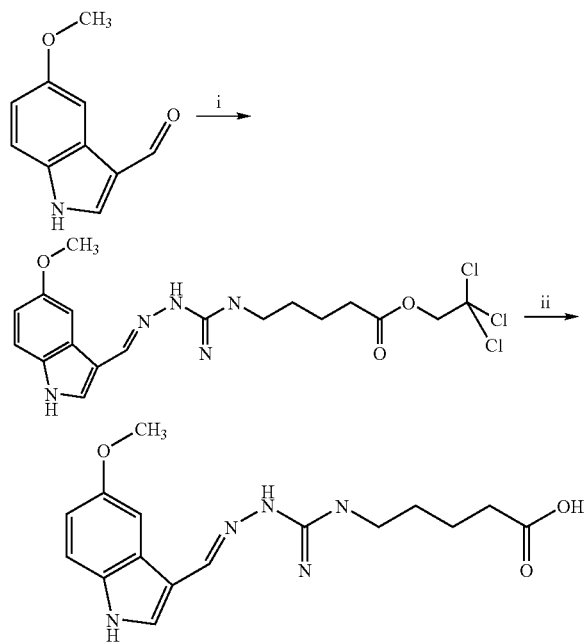

Scheme 3. i, N-2,2,2-(trichloroethyl pentanoate)-N'-aminoguanidine, MeOH/HCl, ii, Zn, 1 M $KH_2PO_4$/THF Example 57

In Vitro Biological Testing of Hydrophilic 5-$HT_4$ Ligands in Adenylyl Cyclase Assays Materials and Methods Establishment of HEK293 Cell Lines Stably Expressing Human 5-$HT_{4(b)}$ Receptors The development of HEK293 cell lines stably expressing human 5-$HT_{4(b)}$ receptors was described and published previously (Bach et al. 2001). Briefly, HEK293 cells (ATCC) were grown in Dulbecco's modified Eagle's medium with 10% fetal calf serum and penicillin (100 U/ml) and streptomycin (100 µg/ml). Cells were transfected with plasmid DNA (pcDNA3.1(−) containing human 5-$HT_{4(b)}$ receptor cDNA) using SuperFect Transfection Reagent (QIAGEN) according to the manufacturers protocol. Serial dilutions of transfected cells were plated in 96 well plates containing G418 (geneticin; Amersham) at 0.4 mg/ml, and isolated single colonies of cells transformed to the neomycin-resistant phenotype were expanded and tested for expression of serotonin receptors by measuring serotonin-stimulated adenylyl cyclase activity (Themmen et al. 1993). Transformed cells were always grown in the presence of G418 (0.4 mg/ml). For binding and adenylyl cyclase analysis, stable cell lines were grown and maintained in UltraCULTURE™ general purpose serum-free medium (BioWhittaker, Walkersville, Md., USA), supplemented with L-glutamine (2 mM), penicillin (100 U/ml) and streptomycin (100 µg/ml).

Membrane Preparation for Radioligand Binding and Adenylyl Cyclase Assay

Membranes were prepared from stably transfected HEK293 cells cultured on 150-mm cell culture dishes and grown to 80% confluence in serum-free medium (UltraCULTURE™, BioWhittaker) with penicillin (10 U/ml) and 2 mM L-Glutamine (BioWhittaker). Cells were washed twice with 10 ml ice-cold HBSS, scraped with a rubber policeman in 10 ml ice-cold HBSS and collected by centrifugation at 800 g for 5 min at 4° C. The cell pellet was resuspended in 1 ml/dish ice-cold STE buffer (27% (w/v) sucrose, 50 mM Tris-HCl, pH 7.5 at 20° C., 5 mM EDTA) and homogenized with an Ultra-Turrax (IKA) homogenizer, using five 10 s bursts with 30 s cooling in ice-water between bursts. To remove nuclei, the homogenate was centrifuged at 300 g for 5 min at 4° C. and the supernatant was further centrifuged at 17000 g for 20 min at 4° C. and the supernatant removed. The crude membrane pellet was resuspended with ten strokes of tight fitting pestle B in a Dounce glass-glass homogenizer in 1 ml/dish ice-cold TE (50 mM Tris-HCl, pH 7.5 at RT, 5 mM EDTA). This procedure was repeated twice and the resuspended membranes were finally aliquoted and flash frozen in liquid nitrogen and stored at −70° C. until use.

Radioligand Binding Assay

Binding assays were performed in 96-well, round-bottom microtiter plates with total reaction volumes of 50-200 µl, containing the indicated concentration of [$^3$H]GR113808 with or without competing unlabelled ligand in a binding buffer containing 50 mM Tris-HCl (pH 7.5 at RT), 1 mM EDTA, 5 mM EGTA, 2 mM $MgCl_2$, 1 mM ascorbate, 0.1% BSA and 100 µM GTP. The plates were incubated at 23EC for 60 min and harvested onto UniFilter™-96 GF/C™ (Packard Instrument Co., Meriden, Conn., USA), presoaked in 0.3% polyethyleneimine (Sigma), using a Packard FilterMate Universal Harvester with 96-well format, and washed 4-6 times with approximately 0.25 ml/well of ice-cold buffer, containing 50 mM Tris-HCl (pH 7.0 at RT) and 2 mM $MgCl_2$. The filters were dried and counted at approximately 400% efficiency in a Top-Count liquid scintillation counter (Packard), using 20 µl per filter well of Micro-Scint liquid scintillation cocktail (Packard).

Adenylyl Cyclase Assay

Adenylyl cyclase activity was measured by determining conversion of [α-$^{32}$P]ATP to [$^{32}$P]cAMP in membranes prepared in STE by homogenization of cells grown and washed as described above in a Dounce glass-glass homogenizer by 10 strokes with the tight-fitting pestle. Membranes were kept on ice prior to assay. Adenylyl cyclase activities were measured on 10-µl aliquots in a final volume of 50 µl in the presence of 0.1 mM [α-$^{32}$P]ATP (1-2×10$^6$ cpm/assay), 4 mM $MgCl_2$, 20 µM GTP, 1 mM EDTA, 1 mM [$^3$H]cAMP (ca. 10,000 cpm/assay), 1 µM 3-isobutyl-1-methyl xanthine (IBMX; Sigma), a nucleoside triphosphate regenerating system consisting of 20 mM creatine phosphate (Sigma), 0.2 mg/ml creatine phosphokinase (Sigma) and 40 U/ml myokinase (Sigma) and additives described in the text and figures. When forskolin (Calbiochem, La Jolla, Calif., USA) was used the concentration was 100 µM. Incubations were for 20 min at 32EC. Cyclic AMP formed was quantified by the double column chromatography system of Salomon et al. (1974) as modified by Bockaert et al. (1976).

Analysis of Binding and Adenylyl Cyclase Data

Binding and adenylyl cyclase data were analyzed by non-linear regression using Microsoft Excel with the Solver add-in, using the below equations.

Competitive binding assays—The data were fit to the equation $$Y=a+(b-a)/(1+x/c) \qquad [1]$$

where a is non-specific binding, b is total binding in the absence of competitor, c is $IC_{50}$, and x is the concentration of competitor. Where relevant, relative binding data were obtained by recalculating the data using a=0 and b=100.

Activation of adenylyl cyclase—The data were fit to the equation $$Y = a + (b-a)x/(c+x) \qquad [2]$$

where a is basal adenylyl cyclase activity, b is maximal adenylyl cyclase activity stimulated by the agonist, c is $EC_{50}$, and x is the concentration of agonist.

$IC_{50}$ values from competitive binding assays were converted to Kb values by the method of Cheng and Prusoff (1973).

Protein Measurements

The protein concentrations in the membrane preparations were measured with the Micro BCA Protein Assay Reagent Kit (Pierce, Rockford, Ill., USA) using bovine serum albumin (BSA) as standard.

Radiochemicals

[$^3$H]GR113808 (84 Ci/mmol), [α-$^{32}$P]ATP (400 Ci/mmol) and [$^3$H]cAMP (30-50 Ci/mmol) were from Amersham (Buckinghamshire, England).

Compounds

5-Hydroxytryptamine hydrochloride (5-HT, serotonin) was from Sigma (St. Louis, Mo., USA). GR113808 (1-methyl-1H-indole-3-carboxylic acid, [1-[2-[(methylsulfonyl)amino]ethyl]-4-piperidinyl]methyl ester) maleate was from Tocris (Avonmouth, UK). The other compounds tested were synthesized by Drug Discovery Laboratories AS (DDL) (Oslo, Norway).

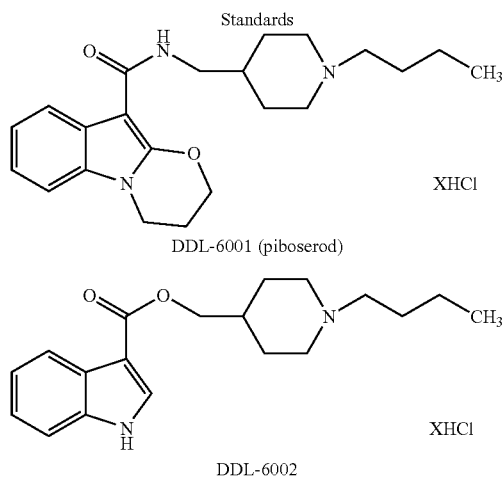

Results of in vitro biological testing of new 5-HT$_4$ ligands in adenylyl cyclase and binding assays, organised per compound (Table 1)

| Substance | Antagonist pK$_b$ value (individual measurements) | Agonist/ Antagonist properties | Binding affinity (pK$_d$ value) (individual measurements) |
|---|---|---|---|
| GR113808 | 9.98, 9.87, 9.77, 9.65, 9.82, 9.75 | Antagonist | 9.94-10.31-10.21-10.71 |
| SB207266 (piboserod) | 9.88, 9.77 | Antagonist | 10.76 |
| DDL-6002 | 9.89 | Antagonist | 10.55-10.66 |
| DDL-6003 | 9.54 | Antagonist | 9.73-10.36 |
| DDL-6004 | 9.00 | Antagonist | 8.76-9.79 |
| DDL-6005 | 6.56 | Antagonist | 6.90 |
| DDL-6006 | n.d. | Unknown | 5.71 |

-continued

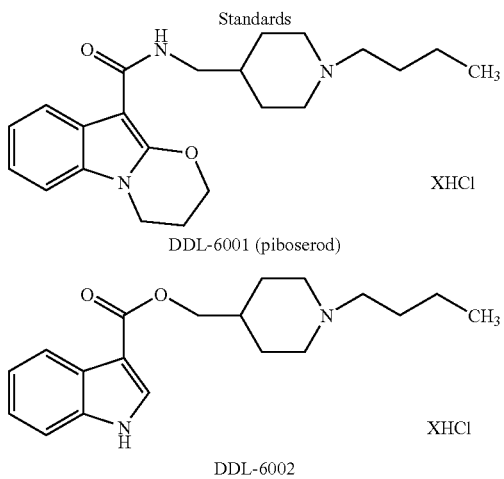

Results of in vitro biological testing of new 5-HT$_4$ ligands in adenylyl cyclase and binding assays, organised per compound (Table 1)

| Substance | Antagonist pK$_b$ value (individual measurements) | Agonist/ Antagonist properties | Binding affinity (pK$_d$ value) (individual measurements) |
|---|---|---|---|
| DDL-6011 | 6.55 | Antagonist | 6.42 |
| DDL-6013 | 8.49 | Weak partial agonist | 7.78 |
| DDL-6014 | 9.95 | Weak partial agonist | 8.53 |
| DDL-6015 | 9.17 | Antagonist | 8.70 |
| DDL-6016 | 8.55 | Weak partial agonist | 8.49 |
| DDL-6021 | 6.24 | Partial agonist | 7.50 |
| DDL-6022 | 6.62-8.31 | Partial agonist | 7.89 |
| DDL-6023 | 5.49-6.95 | Partial agonist | 6.64 |
| DDL-6024 | n.d. | n.d. | 6.35 |
| DDL-6025 | n.d. | n.d | 6.23 |
| DDL-6032 | 8.36 | Partial agonist | 8.19 |
| DDL-6040 | 9.72 | Antagonist | 10.65 |
| DDL-6041 | 9.95 | Antagonist | 10.29 |
| DDL-6042 | 10.14 | Antagonist | 10.81 |
| DDL-6043 | 10.14 | Antagonist | 10.48 |
| DDL-6044 | 9.16 | Antagonist | 9.55 |
| DDL-6045 | 8.47 | Antagonist | 8.84 | n.d. not determined

The invention claimed is:

1. A compound represented by formula IV-P

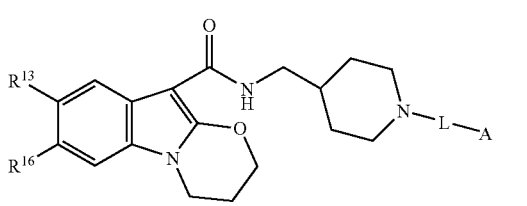

formula IV-P wherein L is absent or selected from the group consisting of straight chain or branched optionally substituted C$_{1-10}$-alkyl, optionally substituted C$_{2-10}$-alkenyl, optionally substituted C$_{2-10}$-alkynyl, C$_{1-10}$-alkylamine, C$_{1-10}$- alkoxy, $C_{2-10}$-alkenyloxy, $C_{2-10}$-alkynyloxy, $C_{1-10}$-alkoxycarbonyl, $C_{2-10}$-alkenyloxycarbonyl, $C_{2-10}$-alkynyloxycarbonyl; and A is selected from the group consisting of —C(O)—OR$^1$, —OP(O)OR$^2$OR$^2$, —P(O)OR$^2$OR$^2$, —SOhd 2OR$^2$, and PO$_3$H; wherein R$^1$ and R$^2$ are independently selected from the group consisting of H, a counter-ion M, $C_{1-15}$-alkyl, $C_{3-8}$-cycloalkyl, aryl, and R$^{1,2}$ wherein R$^{1,2}$ is R'—O—C(O)—R", R'—C(O)—O—R", R'—C(O)—O—R", wherein R' and R" are independently selected from the group consisting of $C_{1-15}$-alkyl, $C_{3-8}$-cycloalkyl and aryl;

R$^{13}$ is selected from the group consisting of H, halogen, NH$_2$, and $C_{1-6}$-alkyl; and R$^{16}$ is selected from the group consisting of H, halogen, OH, O—$C_{1-6}$-alkyl, and $C_{1-6}$-alkyl.

2. A method of treating a cardiovascular disorder in an individual in need thereof, comprising administering a therapeutically effective amount of the compound of claim 1, or a pharmaceutically acceptable salt thereof, to said individual.

3. A method of treating a gastrointestinal disorder in an individual in need thereof, comprising administering a therapeutically effective amount of the compound of claim 1, or a pharmaceutically acceptable salt thereof, to said individual.

4. The method of claim 2, wherein the cardiovascular disorder is selected from the group consisting of tachycardia, bradycardia, cardioexcitation, cardiodepression, arrhythmia, fibrillation, atrial fibrillation, Paroxysmal Supraventricular Tachycardia (PSVT), thromoembolisms and VTE.

5. The method of claim 3, wherein the gastrointestinal disorder is selected from the group consisting of irritable bowel syndrome, gastrointestinal hypomotility disordersugastro-esophageal reflux, heartburn, mild oesophagitis, functional or nonulcer dyspensia, gastroparesis, nausea, vomiting, early satiety in the elderly, paraneoplastic of HIV-associated gastroparesis, drug-induced delays in gastric emptying, functional bowel obstructions, bowel obstructions caused by pancreatic cancer or drugs, and emesis.

6. A method of treating a lower urinary tract disorder in an individual in need thereof comprising administering the compound of claim 1, or a pharmaceutically acceptable salt thereof, to said individual.

7. A pharmaceutical composition, comprising:

a compound according to claim 1; and a pharmaceutically acceptable excipient.

\* \* \* \* \*

UNITED STATES PATENT AND TRADEMARK OFFICE
CERTIFICATE OF CORRECTION

| | | |
|---|---|---|
| PATENT NO. | : 7,834,010 B2 | Page 1 of 1 |
| APPLICATION NO. | : 10/583829 | |
| DATED | : November 16, 2010 | |
| INVENTOR(S) | : Klaveness et al. | |

It is certified that error appears in the above-identified patent and that said Letters Patent is hereby corrected as shown below:

In the Claims:

Claim 1, Column 59, Line 5, delete "-SOhd 2OR$^2$," and replace it with -- -SO$_2$OR$^2$, --.

Claim 1, Column 59, Line 9, delete "R'-C(O)-O-R" and replace it with -- R'-O-C(O)-O-R" --.

Claim 5, Column 60, Line 10, delete "dyspensia" and replace it with -- dyspepsia --.

Signed and Sealed this
Twenty-third Day of August, 2011

David J. Kappos
*Director of the United States Patent and Trademark Office*